(12) United States Patent
Funderburk et al.

(10) Patent No.: US 8,029,442 B2
(45) Date of Patent: Oct. 4, 2011

(54) SENSOR INSERTER ASSEMBLY

(75) Inventors: Jeffery V. Funderburk, Fremont, CA (US); Duane O. Yamasaki, El Cerrito, CA (US); Brian Vanhiel, Marietta, GA (US); Stephen J. Flynn, Peachtree City, GA (US); Bradley D. Kelemen, Longmont, CO (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 11/899,917

(22) Filed: Sep. 6, 2007

(65) Prior Publication Data

US 2008/0004512 A1    Jan. 3, 2008

Related U.S. Application Data

(63) Continuation of application No. 10/703,214, filed on Nov. 5, 2003, now Pat. No. 7,381,184.

(60) Provisional application No. 60/424,099, filed on Nov. 5, 2002.

(51) Int. Cl.
    *A61B 5/00*    (2006.01)
(52) U.S. Cl. .................. 600/365; 600/300; 600/309
(58) Field of Classification Search .................. 600/365, 600/584
    See application file for complete search history.

(56) References Cited

U.S. PATENT DOCUMENTS

| | | |
|---|---|---|
| 3,260,656 A | 7/1966 | Ross, Jr. |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,055,175 A | 10/1977 | Clemens et al. |

(Continued)

FOREIGN PATENT DOCUMENTS

DE    29 03 216    8/1979

(Continued)

OTHER PUBLICATIONS

"Request for Reexamination No. 90-118457 of U.S. Patent No. 6,990,366."

(Continued)

*Primary Examiner* — Patricia Mallari
(74) *Attorney, Agent, or Firm* — Jackson & Co., LLP

(57) ABSTRACT

An analyte monitor includes a sensor, a sensor control unit, and a display unit. The sensor control unit typically has a housing adapted for placement on skin and is adapted to receive a portion of an electrochemical sensor. The sensor control unit also includes two or more conductive contacts disposed on the housing and configured for coupling to two or more contact pads on the sensor. A transmitter is disposed in the housing and coupled to the plurality of conductive contacts for transmitting data obtained using the sensor. The display unit has a receiver for receiving data transmitted by the transmitter of the sensor control unit and a display coupled to the receiver for displaying an indication of a level of an analyte, such as blood glucose. An inserter having a retractable introducer is provided for subcutaneously implanting the sensor in a predictable and reliable fashion.

28 Claims, 27 Drawing Sheets

U.S. PATENT DOCUMENTS

| | | | |
|---|---|---|---|
| 4,059,406 A | 11/1977 | Fleet | |
| 4,076,596 A | 2/1978 | Connery et al. | |
| 4,098,574 A | 7/1978 | Dappen | |
| 4,100,048 A | 7/1978 | Pompei et al. | |
| 4,129,128 A | 12/1978 | McFarlane | |
| 4,151,845 A | 5/1979 | Clemens | |
| 4,168,205 A | 9/1979 | Danninger et al. | |
| 4,172,770 A | 10/1979 | Semersky et al. | |
| 4,178,916 A | 12/1979 | McNamara | |
| 4,206,755 A | 6/1980 | Klein | |
| 4,224,125 A | 9/1980 | Nakamura et al. | |
| 4,240,438 A | 12/1980 | Updike et al. | |
| 4,247,297 A | 1/1981 | Berti et al. | |
| 4,340,458 A | 7/1982 | Lerner et al. | |
| 4,352,960 A | 10/1982 | Dormer et al. | |
| 4,356,074 A | 10/1982 | Johnson | |
| 4,365,637 A | 12/1982 | Johnson | |
| 4,366,033 A | 12/1982 | Richter et al. | |
| 4,375,399 A | 3/1983 | Havas et al. | |
| 4,384,586 A | 5/1983 | Christiansen | |
| 4,390,621 A | 6/1983 | Bauer | |
| 4,401,122 A | 8/1983 | Clark, Jr. | |
| 4,404,066 A | 9/1983 | Johnson | |
| 4,418,148 A | 11/1983 | Oberhardt | |
| 4,427,770 A | 1/1984 | Chen et al. | |
| 4,431,004 A | 2/1984 | Bessman et al. | |
| 4,436,094 A | 3/1984 | Cerami | |
| 4,440,175 A | 4/1984 | Wilkins | |
| 4,450,842 A | 5/1984 | Zick et al. | |
| 4,458,686 A | 7/1984 | Clark, Jr. | |
| 4,461,691 A | 7/1984 | Frank | |
| 4,469,110 A | 9/1984 | Slarna | |
| 4,477,314 A | 10/1984 | Richter et al. | |
| 4,484,987 A | 11/1984 | Gough | |
| 4,522,690 A | 6/1985 | Venkatsetty | |
| 4,524,114 A | 6/1985 | Samuels et al. | |
| 4,526,661 A | 7/1985 | Steckhan et al. | |
| 4,534,356 A | 8/1985 | Papadakis | |
| 4,538,616 A | 9/1985 | Rogoff | |
| 4,543,955 A | 10/1985 | Schroeppel | |
| 4,545,382 A | 10/1985 | Higgins et al. | |
| 4,552,840 A | 11/1985 | Riffer | |
| 4,560,534 A | 12/1985 | Kung et al. | |
| 4,571,292 A | 2/1986 | Liu et al. | |
| 4,573,994 A | 3/1986 | Fischell et al. | |
| 4,581,336 A | 4/1986 | Malloy et al. | |
| 4,595,011 A | 6/1986 | Phillips | |
| 4,619,754 A | 10/1986 | Niki et al. | |
| 4,627,445 A | 12/1986 | Garcia et al. | |
| 4,627,908 A | 12/1986 | Miller | |
| 4,633,878 A | 1/1987 | Bombardieri | |
| 4,637,403 A | 1/1987 | Garcia et al. | |
| 4,650,547 A | 3/1987 | Gough | |
| 4,654,197 A | 3/1987 | Lilja et al. | |
| 4,655,880 A | 4/1987 | Liu | |
| 4,655,885 A | 4/1987 | Hill et al. | |
| 4,671,288 A | 6/1987 | Gough | |
| 4,679,562 A | 7/1987 | Luksha | |
| 4,680,268 A | 7/1987 | Clark, Jr. | |
| 4,682,602 A | 7/1987 | Prohaska | |
| 4,684,537 A | 8/1987 | Graetzel et al. | |
| 4,685,463 A | 8/1987 | Williams | |
| 4,703,756 A | 11/1987 | Gough et al. | |
| 4,711,245 A | 12/1987 | Higgins et al. | |
| 4,717,673 A | 1/1988 | Wrighton et al. | |
| 4,721,601 A | 1/1988 | Wrighton et al. | |
| 4,721,677 A | 1/1988 | Clark, Jr. | |
| 4,726,378 A | 2/1988 | Kaplan | |
| 4,726,716 A | 2/1988 | McGuire | |
| 4,731,726 A | 3/1988 | Allen, III | |
| 4,757,022 A | 7/1988 | Shults et al. | |
| 4,758,323 A | 7/1988 | Davis et al. | |
| 4,759,371 A | 7/1988 | Franetzki | |
| 4,759,828 A | 7/1988 | Young et al. | |
| 4,764,416 A | 8/1988 | Ueyama et al. | |
| 4,776,944 A | 10/1988 | Janata et al. | |
| 4,781,798 A | 11/1988 | Gough | |
| 4,784,736 A | 11/1988 | Lonsdale et al. | |
| 4,795,707 A | 1/1989 | Niiyama et al. | |
| 4,796,634 A | 1/1989 | Huntsman et al. | |
| 4,805,624 A | 2/1989 | Yao et al. | |
| 4,813,424 A | 3/1989 | Wilkins | |
| 4,815,469 A | 3/1989 | Cohen et al. | |
| 4,820,399 A | 4/1989 | Senda et al. | |
| 4,822,337 A | 4/1989 | Newhouse et al. | |
| 4,830,959 A | 5/1989 | McNeil et al. | |
| 4,832,797 A | 5/1989 | Vadgama et al. | |
| RE32,947 E | 6/1989 | Dormer et al. | |
| 4,840,893 A | 6/1989 | Hill et al. | |
| 4,848,351 A | 7/1989 | Finch | |
| 4,871,351 A | 10/1989 | Feingold | |
| 4,871,440 A | 10/1989 | Nagata et al. | |
| 4,874,500 A | 10/1989 | Madou et al. | |
| 4,890,620 A | 1/1990 | Gough | |
| 4,894,137 A | 1/1990 | Takizawa et al. | |
| 4,897,162 A | 1/1990 | Lewandowski et al. | |
| 4,897,173 A | 1/1990 | Nankai et al. | |
| 4,909,908 A | 3/1990 | Ross et al. | |
| 4,911,794 A | 3/1990 | Parce et al. | |
| 4,917,800 A | 4/1990 | Lonsdale et al. | |
| 4,919,141 A | 4/1990 | Zier et al. | |
| 4,919,767 A | 4/1990 | Vadgama et al. | |
| 4,923,586 A | 5/1990 | Katayama et al. | |
| 4,927,516 A | 5/1990 | Yamaguchi et al. | |
| 4,934,369 A | 6/1990 | Maxwell | |
| 4,935,105 A | 6/1990 | Churchouse | |
| 4,935,345 A | 6/1990 | Guilbeau et al. | |
| 4,938,860 A | 7/1990 | Wogoman | |
| 4,944,299 A | 7/1990 | Silvian | |
| 4,950,378 A | 8/1990 | Nagara | |
| 4,953,552 A | 9/1990 | DeMarzo | |
| 4,954,129 A | 9/1990 | Giuliani et al. | |
| 4,969,468 A | 11/1990 | Byers et al. | |
| 4,970,145 A | 11/1990 | Bennetto et al. | |
| 4,974,929 A | 12/1990 | Curry | |
| 4,986,271 A | 1/1991 | Wilkins | |
| 4,994,167 A | 2/1991 | Shults et al. | |
| 5,001,054 A | 3/1991 | Wagner | |
| 5,035,860 A | 7/1991 | Kleingeld et al. | |
| 5,036,860 A * | 8/1991 | Leigh et al. .................. 600/567 |
| 5,050,612 A | 9/1991 | Matsumura | |
| 5,058,592 A | 10/1991 | Whisler | |
| 5,070,535 A | 12/1991 | Hochmair et al. | |
| 5,082,550 A | 1/1992 | Rishpon et al. | |
| 5,082,786 A | 1/1992 | Nakamoto | |
| 5,089,112 A | 2/1992 | Skotheim et al. | |
| 5,095,904 A | 3/1992 | Seligman et al. | |
| 5,101,814 A | 4/1992 | Palti | |
| 5,108,564 A | 4/1992 | Szuminsky et al. | |
| 5,109,850 A | 5/1992 | Blanco et al. | |
| 5,120,420 A | 6/1992 | Nankai et al. | |
| 5,126,034 A | 6/1992 | Carter et al. | |
| 5,133,856 A | 7/1992 | Yamaguchi et al. | |
| 5,135,003 A | 8/1992 | Souma | |
| 5,141,868 A | 8/1992 | Shanks et al. | |
| 5,161,532 A | 11/1992 | Joseph | |
| 5,165,407 A | 11/1992 | Wilson et al. | |
| 5,174,291 A | 12/1992 | Schoonen et al. | |
| 5,190,041 A | 3/1993 | Palti | |
| 5,192,416 A | 3/1993 | Wang et al. | |
| 5,198,367 A | 3/1993 | Aizawa et al. | |
| 5,202,261 A | 4/1993 | Musho et al. | |
| 5,205,920 A | 4/1993 | Oyama et al. | |
| 5,208,154 A | 5/1993 | Weaver et al. | |
| 5,209,229 A | 5/1993 | Gilli | |
| 5,217,595 A | 6/1993 | Smith et al. | |
| 5,229,282 A | 7/1993 | Yoshioka et al. | |
| 5,250,439 A | 10/1993 | Musho et al. | |
| 5,262,035 A | 11/1993 | Gregg et al. | |
| 5,262,305 A | 11/1993 | Heller et al. | |
| 5,264,103 A | 11/1993 | Yoshioka et al. | |
| 5,264,104 A | 11/1993 | Gregg et al. | |
| 5,264,106 A | 11/1993 | McAleer et al. | |
| 5,271,815 A | 12/1993 | Wong | |
| 5,279,294 A | 1/1994 | Anderson et al. | |
| 5,284,156 A * | 2/1994 | Schramm et al. ............. 600/567 |
| 5,286,362 A | 2/1994 | Hoenes et al. | |

| | | | | | | |
|---|---|---|---|---|---|---|
| 5,286,364 A | 2/1994 | Yacynych et al. | | 6,134,461 A | 10/2000 | Say et al. |
| 5,288,636 A | 2/1994 | Pollmann et al. | | 6,143,164 A | 11/2000 | Heller et al. |
| 5,293,546 A | 3/1994 | Tadros et al. | | 6,175,752 B1 * | 1/2001 | Say et al. .................. 600/345 |
| 5,320,098 A | 6/1994 | Davidson | | 6,338,790 B1 | 1/2002 | Feldman et al. |
| 5,320,725 A | 6/1994 | Gregg et al. | | 6,368,141 B1 | 4/2002 | VanAntwerp et al. |
| 5,322,063 A | 6/1994 | Allen et al. | | 6,368,274 B1 | 4/2002 | VanAntwerp et al. |
| 5,337,747 A | 8/1994 | Neftel | | 6,695,860 B1 * | 2/2004 | Ward et al. ................ 606/185 |
| 5,352,348 A | 10/1994 | Young et al. | | 6,746,582 B2 | 6/2004 | Heller et al. |
| 5,356,786 A | 10/1994 | Heller et al. | | 6,936,006 B2 * | 8/2005 | Sabra ....................... 600/300 |
| 5,368,028 A | 11/1994 | Palti | | 7,381,184 B2 | 6/2008 | Funderburk et al. |
| 5,372,133 A | 12/1994 | Hogen Esch | | 2002/0130042 A1 * | 9/2002 | Moerman et al. ........ 204/403.01 |
| 5,376,251 A | 12/1994 | Kaneko et al. | | 2003/0078560 A1 | 4/2003 | Miller et al. |
| 5,378,628 A | 1/1995 | Gratzel et al. | | 2004/0002682 A1 | 1/2004 | Kovelman et al. |
| 5,387,327 A | 2/1995 | Khan | | 2004/0064133 A1 | 4/2004 | Miller et al. |
| 5,390,671 A | 2/1995 | Lord et al. | | 2004/0133164 A1 | 7/2004 | Funderburk et al. |
| 5,391,250 A | 2/1995 | Cheney, II et al. | | 2008/0064941 A1 | 3/2008 | Funderburk et al. |
| 5,395,504 A | 3/1995 | Saurer et al. | | | | |
| 5,400,782 A | 3/1995 | Beaubiah | | FOREIGN PATENT DOCUMENTS | | |
| 5,411,647 A | 5/1995 | Johnson et al. | | DE | 227 029 A3 | 9/1985 |
| 5,431,160 A | 7/1995 | Wilkins et al. | | DE | 3934299 | 10/1990 |
| 5,437,999 A | 8/1995 | Diebold et al. | | EP | 0 010 375 A1 | 4/1980 |
| 5,469,846 A | 11/1995 | Khan | | EP | 0 026 995 A1 | 4/1981 |
| 5,491,474 A | 2/1996 | Suni et al. | | EP | 0 048 090 A2 | 3/1982 |
| 5,494,562 A | 2/1996 | Maley et al. | | EP | 0 078 636 A1 | 5/1983 |
| 5,496,453 A | 3/1996 | Uenoyama et al. | | EP | 0 096 288 A1 | 5/1983 |
| 5,497,772 A | 3/1996 | Schulman et al. | | EP | 0 098 592 | 1/1984 |
| 5,531,878 A | 7/1996 | Vadgama et al. | | EP | 0 125 139 A2 | 11/1984 |
| 5,545,191 A | 8/1996 | Mann et al. | | EP | 0 127 958 A2 | 12/1984 |
| 5,560,357 A | 10/1996 | Faupel et al. | | EP | 0 136 362 A1 | 4/1985 |
| 5,562,713 A | 10/1996 | Silvian | | EP | 0 170 375 A2 | 2/1986 |
| 5,565,085 A | 10/1996 | Ikeda et al. | | EP | 0 177 743 A2 | 4/1986 |
| 5,567,302 A | 10/1996 | Song et al. | | EP | 0 080 304 B1 | 5/1986 |
| 5,568,806 A | 10/1996 | Cheney, II et al. | | EP | 0 184 909 A2 | 6/1986 |
| 5,569,186 A | 10/1996 | Lord et al. | | EP | 0 206 218 A2 | 12/1986 |
| 5,582,184 A | 12/1996 | Erickson et al. | | EP | 0 230 472 A1 | 8/1987 |
| 5,582,697 A | 12/1996 | Ikeda et al. | | EP | 0 241 309 A3 | 10/1987 |
| 5,582,698 A | 12/1996 | Flaherty et al. | | EP | 0 245 073 A2 | 11/1987 |
| 5,586,553 A | 12/1996 | Halili et al. | | EP | 0 278 647 A2 | 8/1988 |
| 5,589,326 A | 12/1996 | Deng et al. | | EP | 0 359 831 A1 | 3/1990 |
| 5,593,852 A | 1/1997 | Heller et al. | | EP | 0 368 209 | 5/1990 |
| 5,596,150 A | 1/1997 | Arndt et al. | | EP | 390 390 A1 | 10/1990 |
| 5,617,851 A | 4/1997 | Lipkovker | | EP | 0 400 918 A1 | 12/1990 |
| 5,628,890 A | 5/1997 | Carter et al. | | EP | 0 453 283 A1 | 10/1991 |
| 5,651,869 A | 7/1997 | Yoshioka et al. | | EP | 0 470 290 A1 | 2/1992 |
| 5,660,163 A | 8/1997 | Schulman et al. | | EP | 0 127 958 B2 | 3/1992 |
| 5,665,222 A | 9/1997 | Heller et al. | | EP | 0 255 291 B1 | 6/1992 |
| 5,670,031 A | 9/1997 | Hintsche et al. | | GB | 1394171 | 5/1975 |
| 5,680,858 A | 10/1997 | Hansen et al. | | GB | 1599241 | 9/1981 |
| 5,682,233 A | 10/1997 | Brinda | | GB | 2 073 891 | 10/1981 |
| 5,695,623 A | 12/1997 | Michel et al. | | GB | 2 154 003 | 2/1988 |
| 5,708,247 A | 1/1998 | McAleer et al. | | GB | 2 204 408 | 11/1988 |
| 5,711,297 A | 1/1998 | Iliff | | GB | 2 254 436 | 10/1992 |
| 5,711,861 A | 1/1998 | Ward et al. | | JP | 54-41191 | 4/1979 |
| 5,711,862 A | 1/1998 | Sakoda et al. | | JP | 55-10581 | 1/1980 |
| 5,741,211 A | 4/1998 | Renirie et al. | | JP | 55-10583 | 1/1980 |
| 5,771,001 A | 6/1998 | Cobb | | JP | 55-10584 | 1/1980 |
| 5,791,344 A | 8/1998 | Schulman et al. | | JP | 55-12406 | 1/1980 |
| 5,800,420 A | 9/1998 | Gross et al. | | JP | 56-163447 | 12/1981 |
| 5,807,375 A | 9/1998 | Gross et al. | | JP | 57-70448 | 4/1982 |
| 5,820,551 A | 10/1998 | Hill et al. | | JP | 60-173457 | 9/1985 |
| 5,820,622 A | 10/1998 | Gross et al. | | JP | 60-173458 | 9/1985 |
| 5,822,715 A | 10/1998 | Worthington et al. | | JP | 60-173459 | 9/1985 |
| 5,827,184 A | 10/1998 | Netherly et al. | | JP | 61-090050 | 5/1986 |
| 5,840,020 A | 11/1998 | Heinonen et al. | | JP | 62-85855 | 4/1987 |
| 5,842,983 A | 12/1998 | Abel et al. | | JP | 62-114747 | 5/1987 |
| 5,885,211 A | 3/1999 | Eppstein et al. | | JP | 63-58149 | 3/1988 |
| 5,899,855 A | 5/1999 | Brown | | JP | 63-128252 | 5/1988 |
| 5,954,643 A | 9/1999 | VanAntwerp et al. | | JP | 63-139246 | 6/1988 |
| 5,954,685 A | 9/1999 | Tierny | | JP | 63-294799 | 12/1988 |
| 5,957,854 A | 9/1999 | Besson et al. | | JP | 63-317757 | 12/1988 |
| 5,964,993 A | 10/1999 | Blubaugh, Jr. et al. | | JP | 63-317758 | 12/1988 |
| 5,971,922 A | 10/1999 | Arita et al. | | JP | 1-114746 | 5/1989 |
| 5,972,199 A | 10/1999 | Heller et al. | | JP | 1-114747 | 5/1989 |
| 6,001,067 A | 12/1999 | Shults et al. | | JP | 1-124060 | 5/1989 |
| 6,024,699 A | 2/2000 | Surwit et al. | | JP | 1-134244 | 5/1989 |
| 6,093,172 A | 7/2000 | Funderburk et al. | | JP | 1-156658 | 6/1989 |
| 6,103,033 A | 8/2000 | Say et al. | | JP | 2-62958 | 3/1990 |
| 6,120,676 A | 9/2000 | Heller et al. | | JP | 2-120655 | 5/1990 |
| 6,122,351 A | 9/2000 | Schlueter, Jr. et al. | | JP | 2-287145 | 11/1990 |

| | | |
|---|---|---|
| JP | 2-310457 | 12/1990 |
| JP | 3-26956 | 2/1991 |
| JP | 3-028752 | 2/1991 |
| JP | 3-202764 | 9/1991 |
| JP | 5-72171 | 3/1993 |
| JP | 5-196595 | 8/1993 |
| JP | 5-190050 | 7/1994 |
| JP | 6-190050 | 7/1994 |
| JP | 7-55757 | 3/1995 |
| JP | 7-72585 | 3/1995 |
| JP | 8-285814 | 11/1996 |
| JP | 8-285815 | 11/1996 |
| JP | 9-21778 | 1/1997 |
| JP | 9-101280 | 4/1997 |
| JP | 9-285459 | 11/1997 |
| JP | 10-170471 | 6/1998 |
| SU | 1281988 A1 | 1/1987 |
| WO | WO 89/05119 | 11/1985 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/15993 | 10/1991 |
| WO | WO 92/13271 | 8/1992 |
| WO | WO 94/20602 | 9/1994 |
| WO | WO 94/27140 | 11/1994 |
| WO | WO 96/30431 | 10/1996 |
| WO | WO 96/35370 | 11/1996 |
| WO | WO 97/02847 | 1/1997 |
| WO | WO 97/19344 | 5/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 2004/028337 A2 | 4/2004 |

OTHER PUBLICATIONS

Abruna, H. D. et al., "*Rectifying Interfaces Using Two-Layer Films of Electrochemically Polymerized Vinylpyridine and Vinylbipyridine Complexes of Ruthenium and Iron on Electrodes*," J. Am. Chem. Soc., 103 (1):1-5 (Jan. 14, 1981).

Albery, W. J. et al., "*Amperometric Enzyme Electrodes*," Phil. Trans. R. Soc. Lond. B316:107-119 (1987).

Albery, W. J. et al., "*Amperometric enzyme electrodes. Part II. Conducting salts as electrode materials for the oxidation of glucose oxidase*," J. Electroanal. Chem. Interfacial Electrochem., 194(2) (1 page—Abstract only) (1985).

Alcock, S. J. et al., "*Continuous Analyte Monitoring to Aid Clinical Practice*," IEEE Engineering in Medicine and Biology, 319-325 (1994).

Anderson, L. B. et al., "*Thin-Layer Electrochemistry: Steady-State Methods of Studying Rate Processes*," J. Electroanal. Chem., 10:295-395 (1965).

Armour, J. et al. "*Application of Chronic Intravascular Blood Glucose Sensor in Dogs*," Diabetes, vol. 39 (Dec. 1990), pp. 1519-1526.

Bartlett, P. N. et al., "*Covalent Binding of Electron Relays to Glucose Oxidation*," J. Chem. Soc. Chem. Commun., 1603-1604 (1987).

Bartlett, P. N. et al., "*Modification of glucose oxidase by tetrathiafulvalene*," J. Chem. Soc., Chem. Commun., 16 (1 page—Abstract only) (1990).

Bindra, D.S. et al., "*Design and in Vitro Studies of a Needle-Type Glucose Sensor for Subcutaneous Monitoring*", Anal. Chem., 63(17):1692-1696 (Sep. 1, 1991).

Bobbioni-Harsch, E. et al., "*Lifespan of subcutaneous glucose sensors and their performances during dynamic glycaemia changes in rats*," J. Biomed. Eng. 15:457-463 (1993).

Brandt, J. et al., "*Covalent attachment of proteins to polysaccharide carriers by means of benzoquinone*," Biochim. Biophys. Acta, 386(1) (1 page Abstract only) (1975).

Brownlee, M. et al., "*A Glucose-Controlled Insulin-Delivery System: Semisynthetic Insulin Bound to Lectin*", Science, 206(4423):1190-1191 (Dec. 7, 1979).

Cass, A.E.G. et al., "*Ferricinum Ion As An Electron Acceptor for Oxido-Reductases*," J. Electroanal. Chem., 190:117-127 (1985).

Cass, A.E.G. et al., "*Ferrocene-Mediated Enzyme Electrode for Amperometric Determination of Glucose*", Anal. Chem., 56(4):667-671 (Apr. 1984).

Castner, J. F. et al., "*Mass Transport and Reaction Kinetic Parameters Determined Electrochemically for Immobilized Glucose Oxidase*," Biochemistry, 23(10):2203-2210 (1984).

Claremont, D.J. et al., "*Biosensors for Continuous in Vivo Glucose Monitoring*", IEEE Engineering in Medicine and Biology Society 10th Annual International Conference, New Orleans, Louisiana, 3 pgs. (Nov. 4-7, 1988).

Clark L.C. et al., "*Differential Anodic Enzyme Polarography for the Measurement of Glucose*", Oxygen Transport to Tissue: Instrumentation, Methods, and Physiology, 127-132 (1973).

Clark, L.C. et al., "*Long-term Stability of Electroenzymatic Glucose Sensors Implanted in Mice*," Trans. Am. Soc. Artif. Intern. Organs, XXXIV:259-265 (1988).

Clark, L.C., Jr. et al., "*Electrode Systems for Continuous Monitoring in Cardiovascular Surgery*," Annals New York Academy of Sciences, pp. 29-45 (1962).

Clarke, W. L., et al., "*Evaluating Clinical Accuracy of Systems for Self-Monitoring of Blood Glucose*," Diabetes Care, 10(5):622-628 (Sep.-Oct. 1987).

Csoregi, E. et al., "*Design and Optimization of a Selective Subcutaneously Implantable Glucose Electrode Based on 'Wired' Glucose Oxidase*," Anal. Chem. 67(7):1240-1244 (Apr. 1, 1995).

Csoregi, E. et al., "*Design, Characterization, and One-Point in Vivo Calibration of a Subcutaneously Implanted Glucose Electrode*," Anal. Chem. 66(19):3131-3138 (Oct. 1, 1994).

Csoregi, E. et al., "*On-Line Glucose Monitoring by Using Microdialysis Sampling and Amperometric Detection Based on "Wired" Glucose Oxidase in Carbon Paste*," Mikrochim. Acta. 121:31-40 (1995).

Davis, G., "*Electrochemical Techniques for the Development of Amperometric Biosensors*", Biosensors, 1:161-178 (1985).

Degani, Y. et al., "*Direct Electrical Communication between Chemically Modified Enzymes and Metal Electrodes. 1. Electron Transfer from Glucose Oxidase to Metal Electrodes via Electron Relays, Bound Covalently to the Enzyme*," J. Phys. Chem. 91(6):1285-1289 (1987).

Degani, Y. et al., "*Direct Electrical Communication between Chemically Modified Enzymes and Metal Electrodes. 2. Methods for Bonding Electron-Transfer Relays to Glucose Oxidase and D-Amino-Acid Oxidase*," J. Am. Chem. Soc., 110(81:2615-2620 (1988).

Degani, Y. et al., "*Electrical Communication between Redox Centers of Glucose Oxidase and Electrodes via Electrostatically and Covalently Bound Redox Polymers*," J. Am. Chem. Soc., 111:2357-2358 (1989).

Denisevich, P. et al., "*Unidirectional Current Flow and Charge State Trapping at Redox Polymer Interfaces on Bilayer Electrodes: Principles, Experimental Demonstration, and Theory*," J. Am. Chem. Soc., 103(16):4727-4737(1981).

Dicks, J. M., "*Ferrocene modified polypyrrole with immobilised glucose oxidase and its application in amperometric glucose microbiosensors*," Ann. Biol. clin., 47:607-619 (1989).

Ellis, C. D., "*Selectivity and Directed Charge Transfer through an Electroactive Metallopolymer Film*," J. Am. Chem. Soc., 103(25):7480-7483 (1981).

Engstrom, R.C. et al., "*Characterization of Electrochemically Pretreated Glassy Carbon Electrodes*", Anal. Chem., 56(2):136-141 (Feb. 1984).

Engstrom, R.C., "*Electrochemical Pretreatment of Glassy Carbon Electrodes*", Anal. Chem., 54 (13):2310-2314 (Nov. 1982).

Feldman, B.J. et al., "*Electron Transfer Kinetics at Redox Polymer/Solution Interfaces Using Microelectrodes and Twin Electrode Thin Layer Cells*", J. Electroanal. Chem., 194(1):63-81 (Oct. 10, 1985).

Fischer, H. et al., "*Intramolecular Electron Transfer Mediated by 4,4'-Bipyridine and Related Bridging Groups*", J. Am. Chem. Soc., 98(18):5512-5517 (Sep. 1, 1976).

Foulds, N.C. et al., "*Enzyme Entrapment in Electrically Conducting Polymers*," J. Chem. Soc., Faraday Trans 1., 82:1259-1264 (1986).

Foulds, N.C. et al., "*Immobilization of Glucose Oxidase in Ferrocene-Modified Pyrrole Polymers*," Anal. Chem., 60(22):2473-2478 (Nov. 15, 1988).

Frew, J.E. et al., "*Electron-Transfer Biosensors*", Phil. Trans. R Soc. Lond., B316:95-106 (1987).

Gorton, L. et al., "*Selective detection in flow analysis based on the combination of immobilized enzymes and chemically modified electrodes*," Analytica Chimica Acta., 250:203-248 (1991).

Gregg, B. A. et al., "*Cross-Linked Redox Gels Containing Glucose Oxidase for Amperometric Biosensor Applications*," Analytical Chemistry, 62(3):258-263 (Feb. 1, 1990).

Gregg, B. A. et al., "*Redox Polymer Films Containing Enzymes. 1. A Redox-Conducting Epoxy Cement: Synthesis, Characterization, and Electrocatalytic Oxidation of Hydroquinone*," J. Phys. Chem., 95(15):5970-5975 (1991).

Hale, P.D. et al., "*A New Class of Amperometric Biosensor Incorporating a Polymeric Electron-Transfer Mediator*," J. Am. Chem. Soc., 111(9):3482-3484 (1989).

Harrison, D.J. et al., "*Characterization of Perfluorosulfonic Acid Polymer Coated Enzyme Electrodes and a Miniaturized Integrated Potentiostat for Glucose Analysis in Whole Blood*", Anal. Chem., 60(19):2002-2007 (Oct. 1, 1988).

Hawkridge, F. M. et al., "*Indirect Coulometric Titration of Biological Electron Transport Components*," Analytical Chemistry, 45(7):1021-1027 (Jun. 1973).

Heller, A., "*Amperometric biosensors based on three-dimensional hydrogel-forming epoxy networks*," Sensors and Actuators B, 13-14:180-183 (1993).

Heller, A., "*Electrical Connection of Enzyme Redox Centers to Electrodes*," J. Phys. Chem., 96 (9):3579-3587 (1992).

Heller, A., "*Electrical Wiring of Redox Enzymes*," Acc. Chem. Res., 23(5):129-134 (1990).

Ianniello, R.M. et al. "*Immobilized Enzyme Chemically Modified Electrode as an Amperometric Sensor*", Anal. Chem., 53(13):2090-2095 (Nov. 1981).

Ianniello, R.M. et al., "*Differential Pulse Voltammetric Study of Direct Electron Transfer in Glucose Oxidase Chemically Modified Graphite Electrodes*", Anal. Chem., 54(7):1098-1101 (Jun. 1981).

Ikeda, T. et al., "*Glucose oxidase-immobilized benzoquinone-carbon paste electrode as a glucose sensor*," Agric. Biol. Chem., 49(2) (1 page—Abstract only) (1985).

Ikeda, T. et al., "*Kinetics of Outer-Sphere Electron Transfers Between Metal Complexes in Solutions and Polymeric Films on Modified Electrodes*", J. Am. Chem. Soc., 103(25):7422-7425 (Dec. 16, 1981).

Johnson, J. M. et al., "*Potential-Dependent Enzymatic Activity in an Enzyme Thin-Layer Cell*," Anal. Chem. 54:1377-1383 (1982).

Johnson, K. W., "*Reproducible Electrodeposition of Biomolecules for the Fabrication of Miniature Electroenzymatic Biosensors*", Sensors and Actuators B Chemical, B5:85-89 (1991).

Jonsson, G. et al., "*An Amperometric Glucose Sensor Made by Modification of a Graphite Electrode Surface With Immobilized Glucose Oxidase and Adsorbed Mediator*", Biosensors, 1:355-368 (1985).

Josowicz, M. et al., "*Electrochemical Pretreatment of Thin Film Platinum Electrodes*", J. Electrochem. Soc., 135(1):112-115 (Jan. 1988).

Katakis, I. et al., "*Electrostatic Control of the Electron Transfer Enabling Binding of Recombinant Glucose Oxidase and Redox Polyelectrolytes*," J. Am. Chem. Soc., 116(8):3617-3618 (1994).

Katakis, I. et al., "*L-.alpha.-Glycerophosphate and L-Lactate Electrodes Based on the Electrochemical "Wiring" of Oxidases*," Analytical Chemistry, 64(9):1008-1013 (May 1, 1992).

Kenausis, G. et al., "*Wiring of glucose oxidase and lactate oxidase within a hydrogel made with poly(vinyl pyridine)complexed with[Os(4,4'-dimethoxy-2,2'-bipyridine).sub.2 Cl].sup.+/2+*," J. Chem. Soc., Faraday Trans., 90(20):4131-4136 (1996).

Koudelka, M. et al., "*In-Vivo Behaviour of Hypodermically Implanted Microfabricated Glucose Sensors*", Biosensors & Bioelectronics, 6(1):31-36 (1991).

Kulys, J. et al., "*Mediatorless peroxidase electrode and preparation of bienzyme sensors*," Bioelectrochemisty and Bioenergetics, 24:305-311 (1990).

Lager, W. et al., "*Implantable Electrocatalytic Glucose Sensor*," Horm. Metab. Res., 26:526-530 (Nov. 1994).

Lindner, E. et al. "*Flexible(Kapton-Based) Microsensor Arrays of High Stability for Cardiovascular Applications*", J. Chem. Soc. Faraday Trans., 89(2):361-367 (Jan. 21, 1993).

Maidan, R. et al., "*Elimination of Electrooxidizable Interferant-Produced Currents in Amperometric Biosensors*," Analytical Chemistry, 64(23):2889-2896 (Dec. 1, 1992).

Mastrototaro, J.J. et al., "*An Electroenzymatic Glucose Sensor Fabricated on a Flexible Substrate*", Sensors and Biosensors B Chemical, B5:139-144 (1991).

McKean, B. et al. "*A Telemetry-Instrumentation System for Chronically Implanted Glucose and Oxygen Sensors*," IEEE Transactions on Biomedical Engineering, vol. 35, No. 7, (Jul. 1988), pp. 526-532.

McNeil, C. J. et al., "*Thermostable Reduced Nicotinamide Adenine Dinucleotide Oxidase: Application to Amperometric Enzyme Assay*," Anal. Chem., 61(1):25-29 (Jan. 1, 1989).

Miyawaki, O. et al., "*Electrochemical and Glucose Oxidase Coenzyme Activity of Flavin Adenine Dinucleotide Covalently Attached to Glassy Carbon at the Adenine Amino Group*", Biochimica et Biophysica Acta. 838:60-68 (1985).

Moatti-Sirat, D. et al., "*Evaluating in vitro and in vivo the inteference of ascorbate and acetaminophen on glucose detection by a needle-type glucose sensor*," Biosensors & Bioelectronics, 7(5):345-352 (1992).

Moatti-Sirat, D. et al., "*Reduction of acetaminophen interference in glucose sensors by a composite Nation membrane: demonstration in rats and man*," Diabetologia, 37(6) (1 page—Abstract only) (Jun. 1994).

Moatti-Sirat, D. et al., "*Towards continuous glucose monitoring: in vivo evaluation of a miniaturized glucose sensor implanted for several days in rat subcutaneous tissue*," Diabetologia, 35(3) (1 page—Abstract only) (Mar. 1992).

Nagy, G. et al., "*A New Type of Enzyme Electrode: The Ascorbic Acid Eliminator Electrode*," Life Sciences, 31(23):2611-2616 (1982).

Nakamura, S. et al., "*Effect of Periodate Oxidation on the Structure and Properties of Glucose Oxidase*," Biochimica et Biophysica Acta., 445:294-308 (1976).

Narazimhan, K. et al., "*p-Benzoquinone activation of metal oxide electrodes for attachment of enzymes*," Enzyme Microb. Technol., 7(6) (1 page—Abstract only) (1985).

Ohara, T. J. et al., ""*Wired" Enzyme Electrodes for Amperometric Determination of Glucose or Lactate in the Presence of Interfering Substances*," Analytical Chemistry, 66(15):2451-2457 (Aug. 1, 1994).

Ohara, T. J. et al., "*Glucose Electrodes Based on Cross-Linked [Os(bpy).sub.2 Cl].sup.+/2+ Complexed Poly(1-vinylimadazole) Films*," Analytical Chemistry, 65(23):3512-3516 (Dec. 1, 1993).

Ohara, T. J., "*Osmium Bipyridyl Redox Polymers Used in Enzyme Electrodes*," Platinum Metals Rev., 39 (2):54-62 (Apr. 1995).

Olievier, C. N. et al., "*In vivo Measurement of Carbon Dioxide Tension with a Miniature Electrode*," Pflugers Arch. 373:269-272 (1978).

Paddock, R. et al., "*Electrocatalytic reduction of hydrogen peroxide via direct electron transfer from pyrolytic graphite electrodes to irreversibly adsorbed cytochrome c peroxidase*," J. Electroanal. Chem., 260:487-494 (1989).

Palleschi, G. et al., "*A Study of Interferences in Glucose Measurements in Blood by Hydrogen Peroxide Based Glucose Probes*", Anal. Biochem., 159:114-121 (1986).

Pankratov, I. et al., "*Sol-gel derived renewable-surface biosensors*," Journal of Electroanalytical Chemistry, 393:35-41 (1995).

Pathak, C. P. et al., "*Rapid Photopolymerization of Immunoprotective Gels in Contact with Cells and Tissue*," J. Am. Chem. Soc., 114(21):8311-8312 (1992).

Pickup, J. C. et al., "*In vivo molecular sensing in diabetes mellitus: an implantable glucose sensor with direct electron transfer*," Diabetologia, 32(3):213-217 (1989).

Pickup, J. et al., "*Potentially-implantable, amperometric glucose sensors with mediated electron transfer: improving the operating stability*," Biosensors, 4(2) (1 page—Abstract only) (1989).

Pickup, J., "*Developing glucose sensors for in vivo use*," Tibtech, 11:285-289 (Jul. 1993).

Pishko, M.V. et al., "*Amperometric Glucose Microelectrodes Prepared Through Immobilization of Glucose Oxidase in Redox Hydrogels*", Anal. Chem., 63(20):2268-2272 (Oct. 15, 1991).

Poitout, V. et al., "*A glucose monitoring system for on line estimation in man of blood glucose concentration using a miniaturized glucose sensor implanted in the subcutaneous tissue and a wearable control unit*," Diabetologia. 36(71 (1 page—Abstract only) (Jul. 1993).

Poitout, V. et al., "*Calibration in dogs of a subcutaneous miniaturized glucose sensor using a glucose meter for blood glucose determination*," Biosensors & Bioelectronics, 7:587-592 (1992).

Poitout, V. et al., "*In vitro and in vivo evaluation in dogs of a miniaturized glucose sensor*," ASAIO Transactions, 37(3) (1 page—Abstract only) (Jul.-Sep. 1991).

Pollak, A. et al., "*Enzyme Immobilization by Condensation Copolymerization into Cross-Linked Polyacrylamide Gels*," J. Am. Chem. Soc., 102(20):6324-6336 (1980).

Reach, G. et al., "*Can Continuous Glucose Monitoring Be Used for the Treatment of Diabetes?*" Analytical Chemistry, 64(6):381-386 (Mar. 15, 1992).

Rebrin, K. et al., "*Automated Feedback Control of Subcutaneous Glucose Concentration in Diabetic Dogs*", Diabetologia, 32(8):573-576 (Aug. 1989).

Sakakida, M. et al., "*Ferrocene-mediate needle-type glucose sensor covered with newly designed biocompatible membrane*," Sensors and Actuators B, 13-14:319-322 (1993).

Samuels, G. J. et al., "*An Electrode-Supported Oxidation Catalyst Based on Ruthenium (IV). pH "Encapsulation" in a Polymer Film*," J. Am. Chem. Soc., 103(2):307-312 (1981).

Sasso, S.V. et al., "*Electropolymerized 1,2-Diaminobenzene as a Means to Prevent Interferences and Fouling and to Stabilize Immobilized Enzyme in Electrochemical Biosensors*", Anal. Chem., 62 (11):1111-1117 (Jun. 1, 1990).

Scheller, F. et al., "*Enzyme electrodes and their application*," Phil. Trans. R. Soc. Lond., B 316:85-94 (1987).

Schmehl, R.H. et al., "*The Effect of Redox Site Concentration on the Rate of Mediated Oxidation of Solution Substrates by a Redox Copolymer Film*", J. Electroanal. Chem., 152:97-109 (Aug. 25, 1983).

Shichiri, M. et al., "*Glycaemic Control in Pancrearetomized Dogs with a Wearable Artificial Endocrine Pancreas*", Diabetologia, 24(3):179-184 (Mar. 1983).

Shichiri, M. et al., "*Needle-type Glucose Sensor for Wearable Artificial Endocrine Pancreas*" in Ko et al. (eds.) "*Implantable Sensors for Closed-Loop Prosthetic Systems*" Futura Pub. Co., Inc., 1985) Chapter 15, pp. 197-210.

Shichiri, M. et al., "*Telemetry Glucose Monitoring Device with Needle-type Glucose Sensor: A Useful Tool for Blood Glucose Monitoring in Diabetic Individuals*," Diabetes Care, vol. 9, No. 3 (May-Jun. 1986), pp. 298-301.

Shults, M. "*A Telemetry-Instrumentation System for Monitoring Multiple Subcutaneously Implanted Glucose Sensors*," IEEE Transactions on Biomedical Engineering, vol. 41, No. 10 (Oct. 1994), pp. 937-942.

Sittampalam, G. et al., "*Surface-Modified Electrochemical Detector for Liquid Chromatography*", Anal. Chem., 55(9):1608-1610 (Aug. 1983).

Soegijoko, S. et al., Horm. Metabl. Res., Suppl. Ser. 12 (1 page—Abstract only) (1982).

Sprules, S. D. et al., "*Evaluation of a New Disposable Screen-Printed Sensor Strip for the Measurement of NADH and Its Modification to Produce a Lactate Biosensor Employing Microliter Volumes*," Electroanalysis, 8(6):539-543 (1996).

Sternberg, F. et al., "*Calibration Problems of Subcutaneous Glucosensors when Applied"In-Situ" in Man*," Horm. metabl. Res. 26:524-525 (1994).

Sternberg, R. et al., "*Covalent Enzyme Coupling on Cellulose Acetate Membranes for Glucose Sensor Development*," Analytical Chemistry, 60(24):2781-2786 (Dec. 15, 1998).

Sternberg, R. et al., "*Study and Development of Multilayer Needle-type Enzyme-based Glucose Microsensors*," Biosensors, 4:27-40 (1988).

Suekane, M., "*Immobilization of glucose isomerase*," Zeitschrift fur Allgemeine Mikrobiologie, 22 (8):565-576 (1982).

Tajima, S. et al., "*Simultaneous Determination of Glucose and 1,5-Anydroglucitol*", Chemical Abstracts, 111(25):394 111:228556g (Dec. 18, 1989).

Tarasevich, M.R. "*Bioelectrocatalysis*", Comprehensive Treatise of Electrochemistry, 10 (Ch. 4):231-295 (1985).

Tatsuma, T. et al., "*Enzyme Monolayer- and Bilayer-Modified Tin Oxide Electrodes for the Determination of Hydrogen Peroxide and Glucose*," Anal. Chem., 61(21):2352-2355 (Nov. 1, 1989).

Taylor, C. et al., "'*Wiring' of glucose oxidase within a hydrogel made with polyvinyl imidazole complexed with[(OS-4,4'-dimethoxy-2,2'-bipyridine)Cl].sup.+/2+*," Journal of Electroanalytical Chemistry, 396:511-515 (1995).

Trojanowicz, M. et al., "*Enzyme Entrapped Polypyrrole Modified Electrode for Flow-Injection Determination of Glucose*," Biosensors & Bioelectronics, 5:149-156 (1990).

Turner, A.P.F. et al., "*Diabetes Mellitus: Biosensors for Research and Management*", Biosensors, 1:85-115 (1985).

Turner, R.F.B. et al., "*A Biocompatible Enzyme Electrode for Continuous in vivo Glucose Monitoring in Whole Blood*," Sensors and Actuators, B1(1-6):561-564 (Jan. 1990).

Tuzhi, P. et al., "*Constant Potential Pretreatment of Carbon Fiber Electrodes for in Vivo Electrochemistry*", Analytical Letters, 24(6):935-945 (1991).

Umaha, M., "*Protein-Modified Electrochemically Active Biomaterial Surface*," U.S. Army Research Office Report, (12 pages) (Dec. 1988).

Updike, S. et al., "*Principles of Long-term Fully Implanted Sensors with Emphasis on Radiotelemetric Monitoring of Blood Glucose from Inside a Subcataneous Foreign Body Capsule(FBC)*" in "*Biosensors in the Body: Continuous in vivo Monitoring*" (John Wiley & Sons, Ltd., 1997) Chapter 4, pp. 117-137.

Urban, G. et al., "*Miniaturized Thin-Film Biosensors Using Covalently Immobilized Glucose Oxidase*", Biosensors & Bioelectronics, 6(7):555-562 (1991).

Velho, G. et al., "*In Vitro and in Vivo Stability of Electrode Potentials in Needle-Type Glucose Sensors*", Diabetes, 38(2):164-171 (Feb. 1989).

Velho, G. et al., "*Strategies for calibrating a subcutaneous glucose sensor*," Biomed. Biochim. Acta, 48 (11/12);957-964 (1989).

Von Woedtke, T. et al., "*In Situ Calibration of Implanted Electrochemical Glucose Sensors*," Biomed. Biochim. Acta, 48(11/12):943-952 (1989).

Vrecke, M. S. et al., "*Chapter 15: Hydrogen Peroxide Electrodes Based on Electrical Connection of Redox Centers of Various Peroxidases to Electrodes through a Three-Dimensional Electron-Relaying Polymer Network*," Diagnostic Biosensor Polymers, 7 pgs. (Jul. 26, 1993).

Wang, D. L. et al., "*Miniaturized Flexible Amperometric Lactate Probe*," Analytical Chemistry, 65 (8):1069-1073 (Apr. 15, 1993).

Wang, J. et al., "*Activation of Glassy Carbon Electrodes by Alternating Current Electrochemical Treatment*", Analytica Chimica Acta, 167:325-334 (Jan. 1985).

Wang, J. et al., "*Amperometric biosensing of organic peroxides with peroxidase-modified electrodes*," Analytica Chimica Acta. 254:81-88 (1991).

Wang, J. et al., "*Screen-Printable Sol-Gel Enzyme-Containing Carbon Inks*," Analytical Chemistry, 68 (15):2705-2708 (Aug. 1, 1996).

Wang, J. et al., "*Sol-Gel-Derived Metal-Dispersed Carbon Composite Amperometric Biosensors*," Electroanalysis, 9(1):52-55 (1997).

Williams, D.L. et al., "*Electrochemical-Enzymatic Analysis of Blood Glucose and Lactate*", Anal. Chem., 42(1):118-121 (Jan. 1970).

Wilson, G. S. et al., "*Progress toward the Development of an Implantable Sensor for Glucose*," Clinical Chemistry, 38(9):1613-1617 (1992).

Yabuki, S. et al., "*Electro-conductive Enzyme Membrane*," J. Chem. Soc. Commun, 945-946 (1989).

Yang, L. et al., "*Determination of Oxidase Enzyme Substrates Using Cross-Flow Thin-Layer Amperometry*," Electroanalysis, 8(8-9):716-721 (1996).

Yao, S.J. et al., "*The Interference of Ascorbate and Urea in Low-Potential Electrochemical Glucose Sensing*", Proceedings of the Twelfth Annual International Conference of the IEEE Engineering in Medicine and Biology Society, 12(2):487-489 (Nov. 1-4, 1990).

Yao, T. et al., "*A Chemically-Modified Enzyme Membrane Electrode As An Amperometric Glucose Sensor*," Analytica Chimica Acta., 148:27-33 (1983).

Ye, L. et al., "*High Current Density "Wired" Quinoprotein Glucose Dehydrogenase Electrode*," Anal. Chem., 65(3):238-241 (Feb. 1, 1993).

Yildiz, A. et al., "*Evaluation of an Improved Thin-Layer Electrode*," Analytical Chemistry, 40 (70):1018-1024 (Jun. 1968).

Zamzow, K. et al., New Wearable Continuous Blood Glucose Monitor (BGM) and Artificial Pancreas (AP), Diabetes, 39:5A(20) (May 1990).

Zhang, Y. et al., "*Application of cell culture toxicity tests to the development of implantable biosensors*," Biosensors & Bioelectronics, 6:653-661 (1991).

Zhang, Y. et al., "*Elimination of the Acetaminophen Interference in an Implantable Glucose Sensor*," Anal. Chem. 66:1183-1188 (1994).

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Sakakida, M., et al., "Development of Ferrocene-Mediated Needle-Type Glucose Sensor as Measure of True Subcutaneous Tissue Glucose Concentrations", *Artificial Organs Today*, vol. 2, No. 2, 1992, pp. 145-158.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Wearable Artificial Endocrine Pancreas With Needle-Type Glucose Sensor", *The Lancet*, 1982, pp. 1129-1131.

Reexamination U.S. Appl. No. 90/008,457, Request for Reexamination of U.S. Patent No. 6,990,366, filed Jan. 23, 2007.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

\* cited by examiner

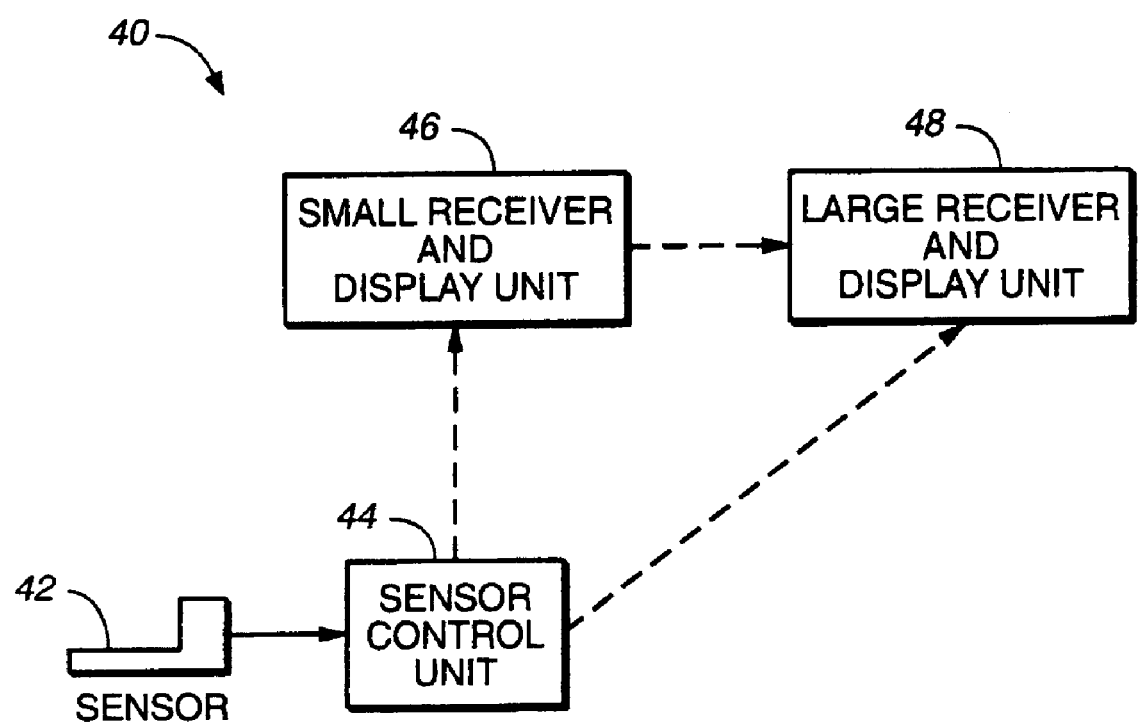
FIG._1

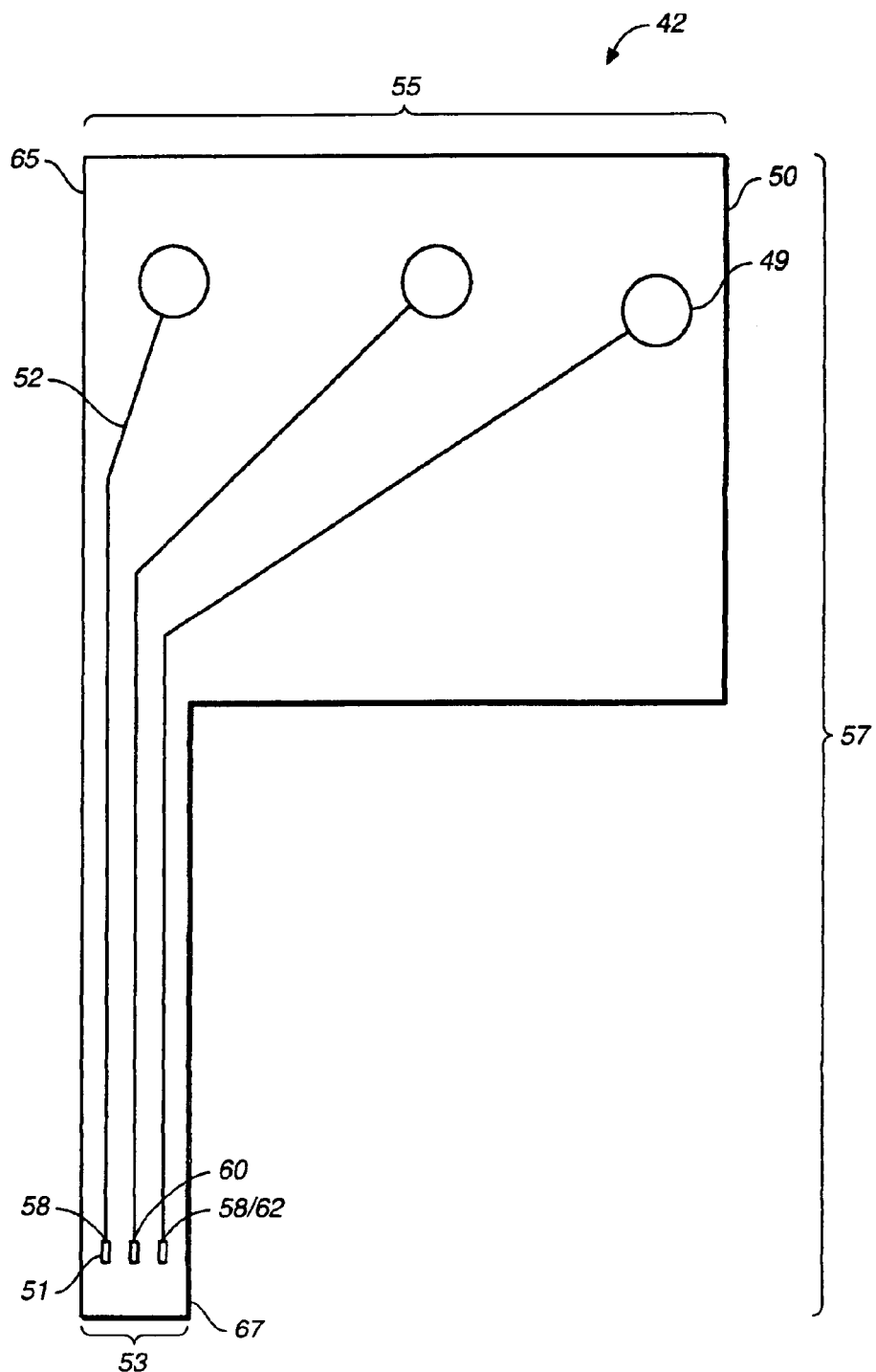
FIG._2

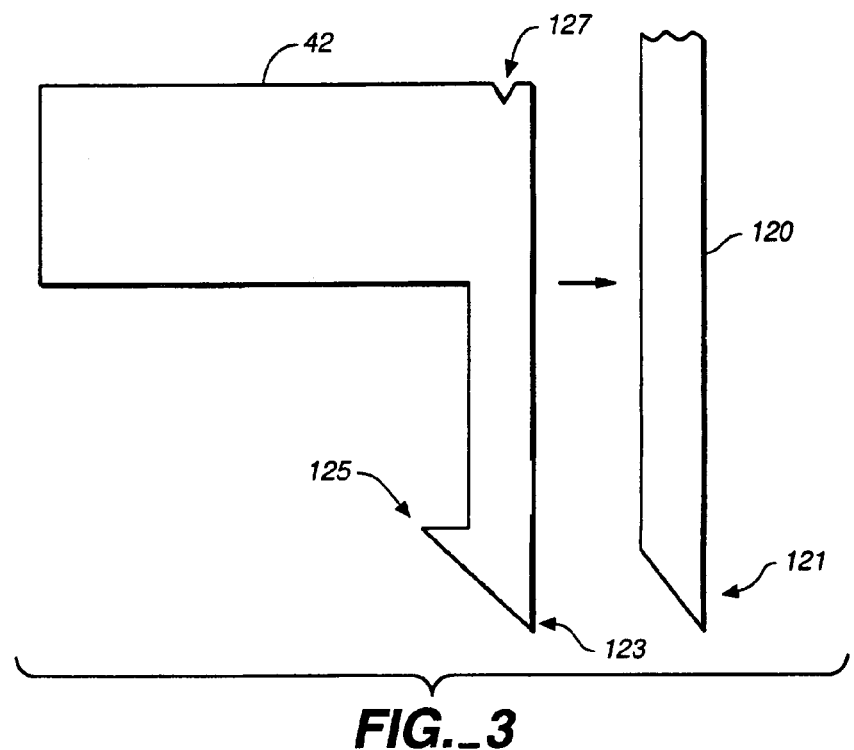
FIG._3
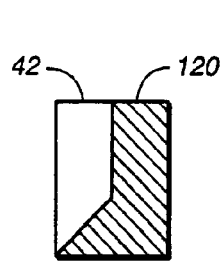
FIG._4A
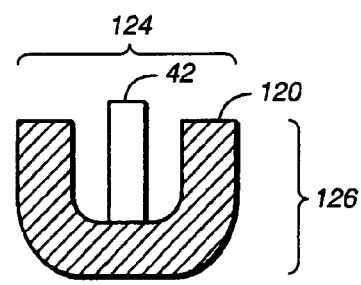
FIG._4B
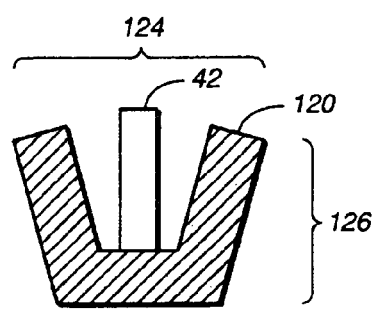
FIG._4C

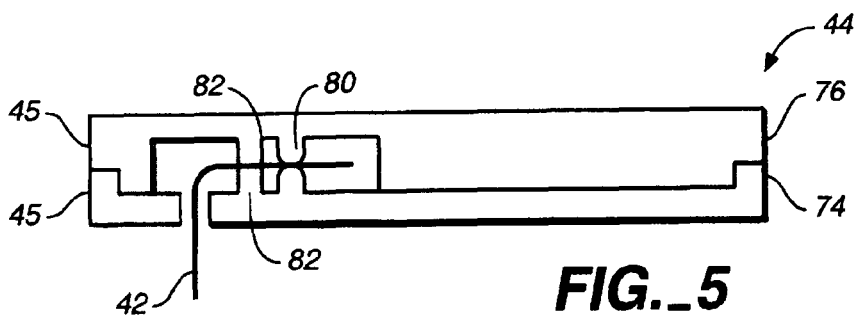
FIG._5
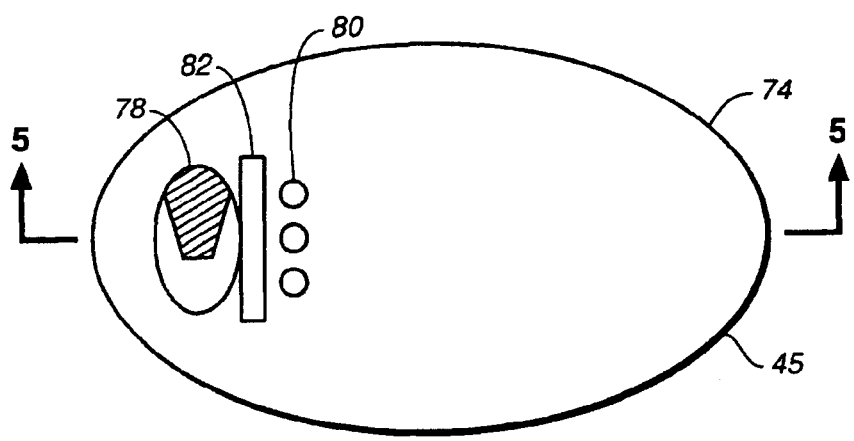
FIG._6
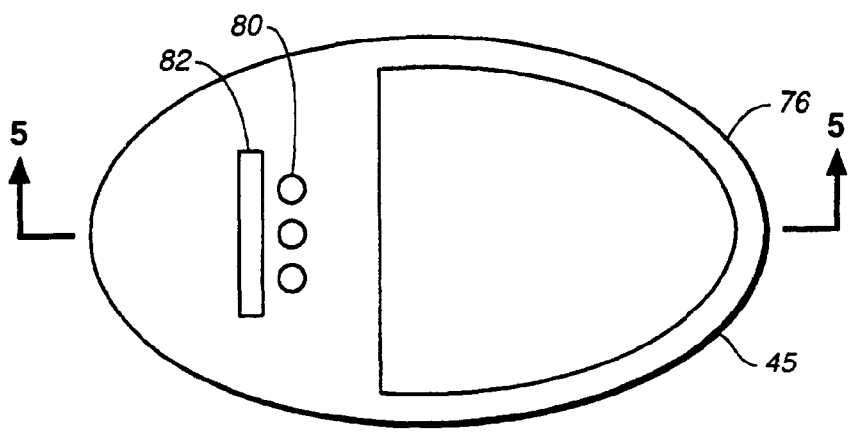
FIG._7

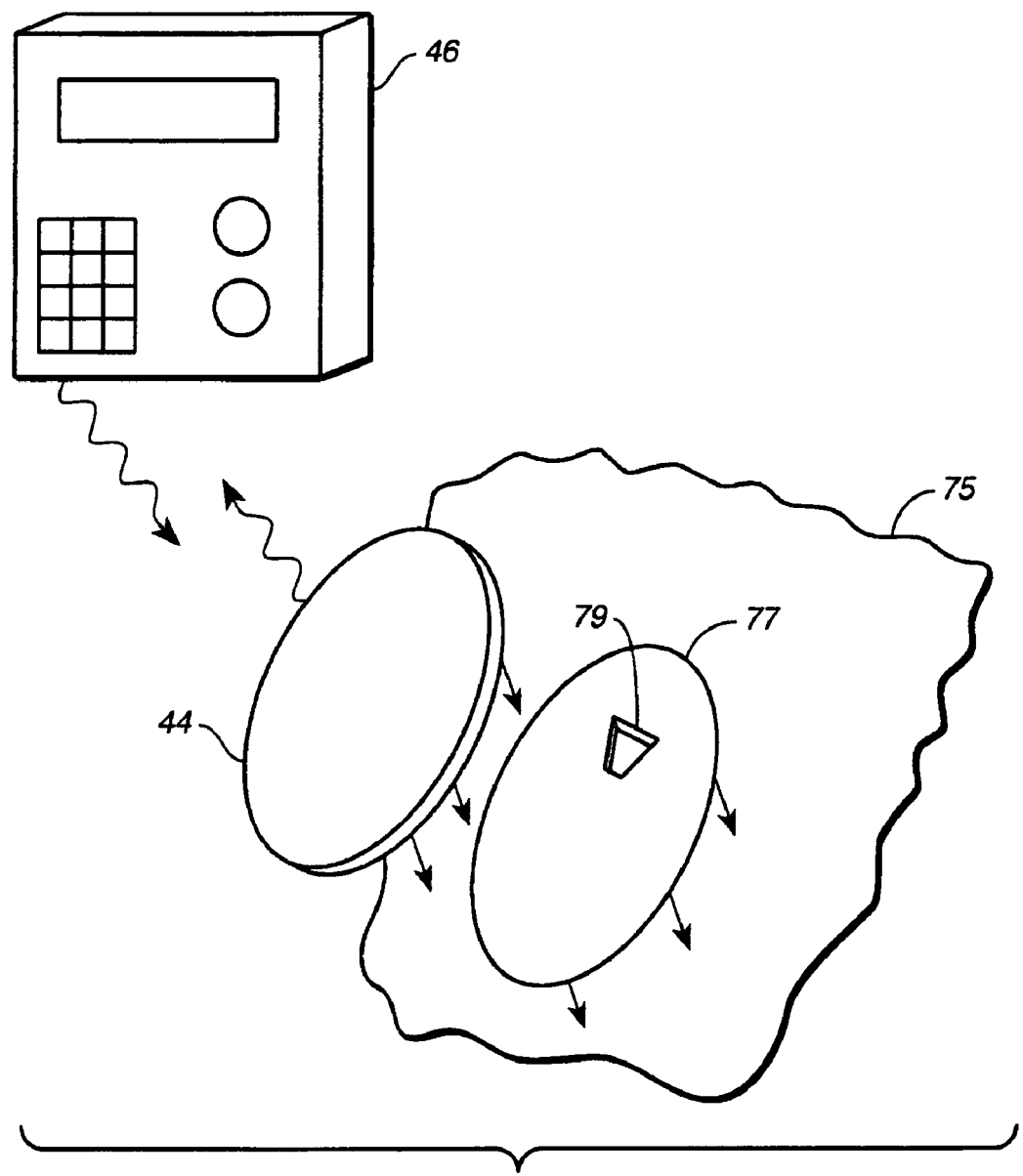
FIG._8

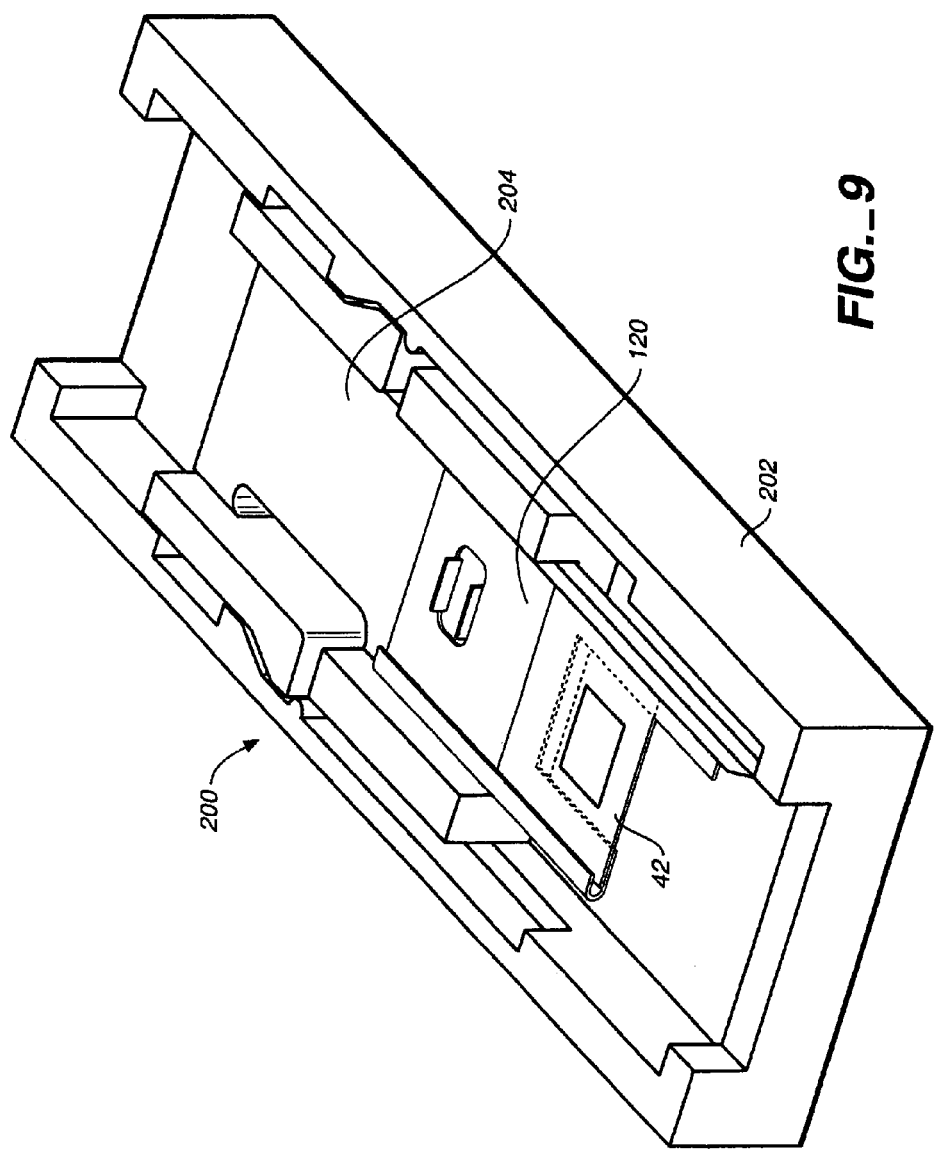
FIG._9

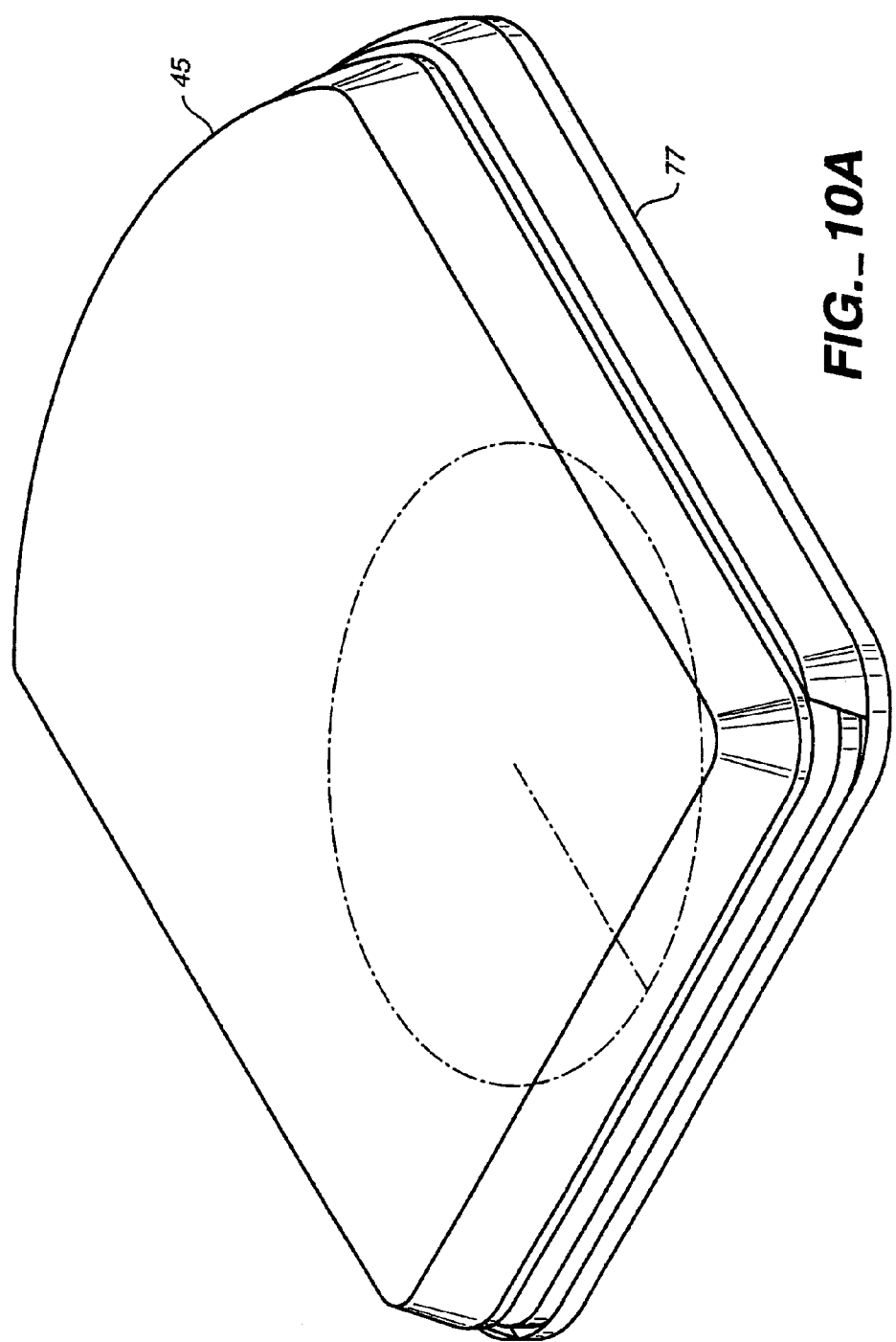

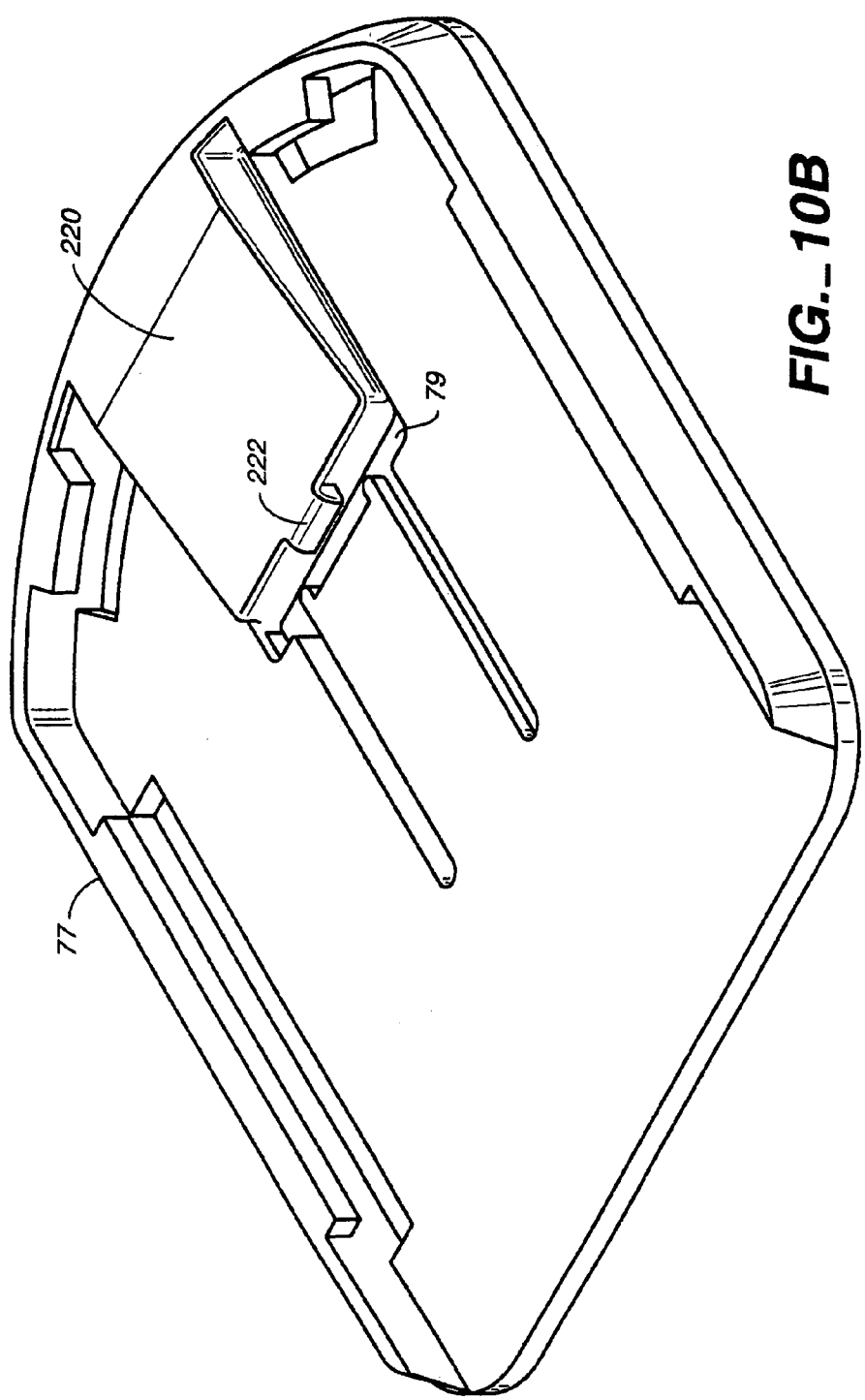
FIG._10B

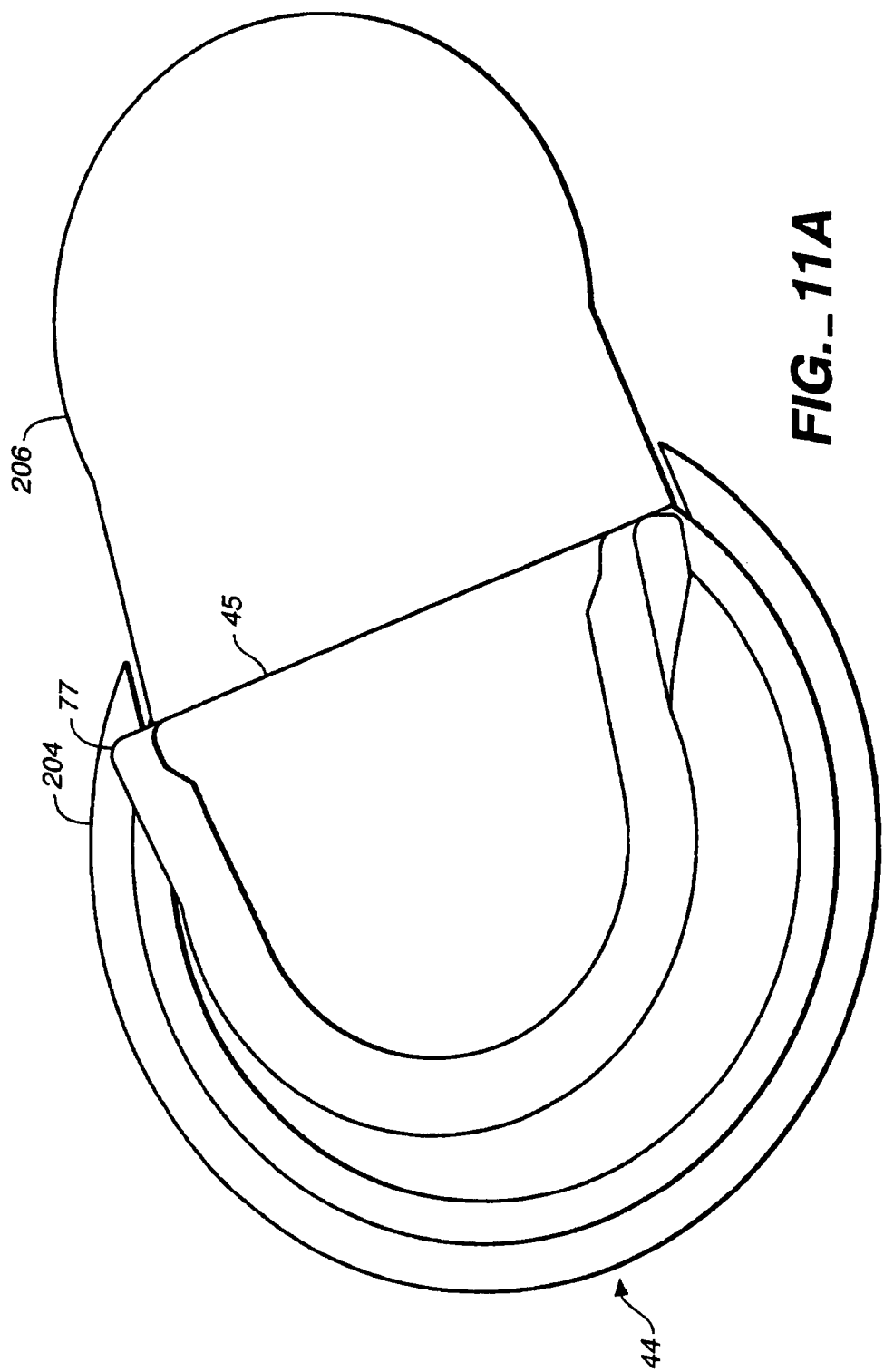

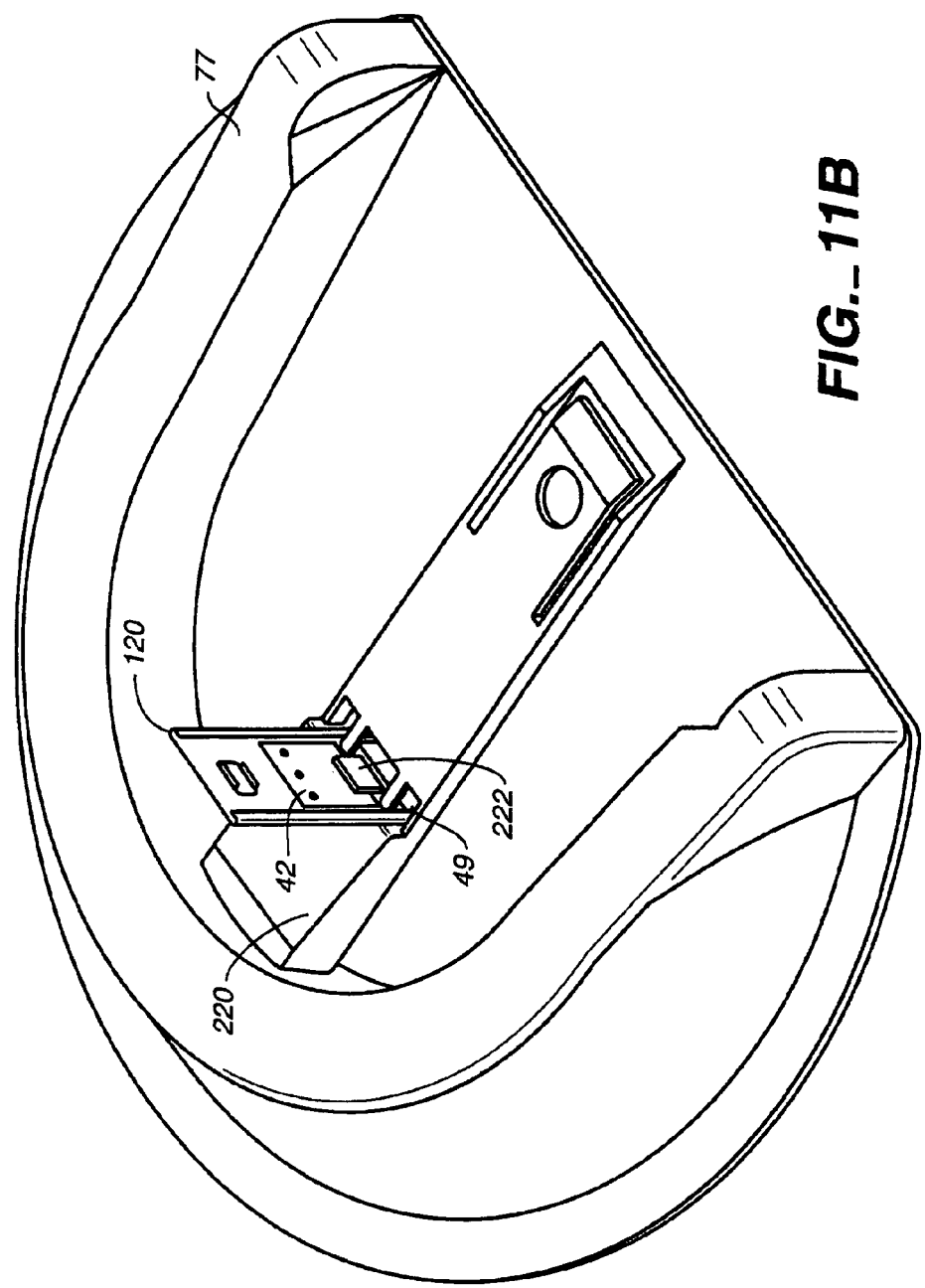
FIG._11B

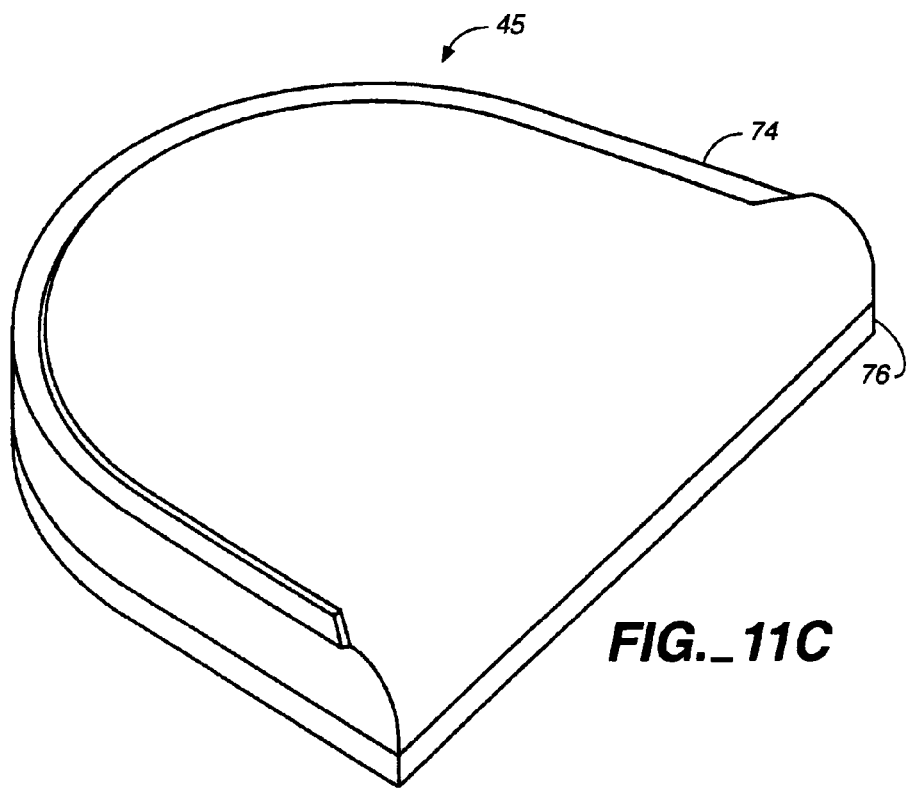
FIG._11C
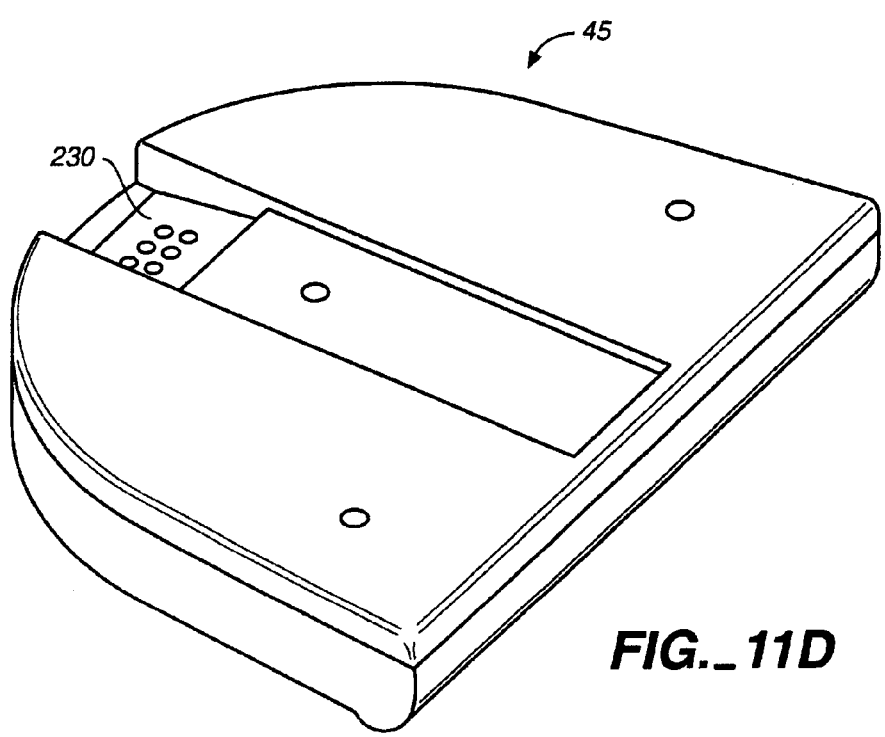
FIG._11D

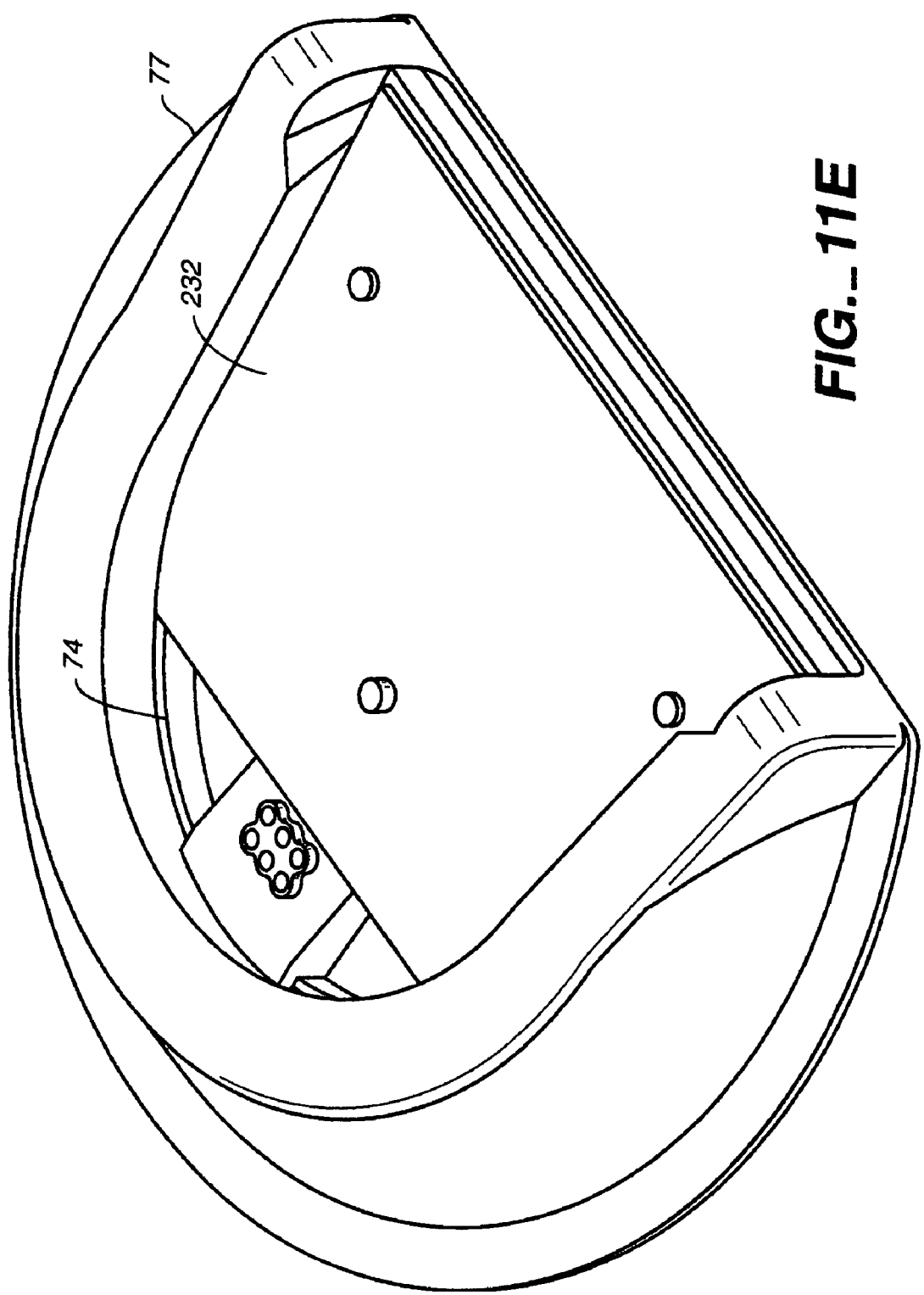
FIG._11E

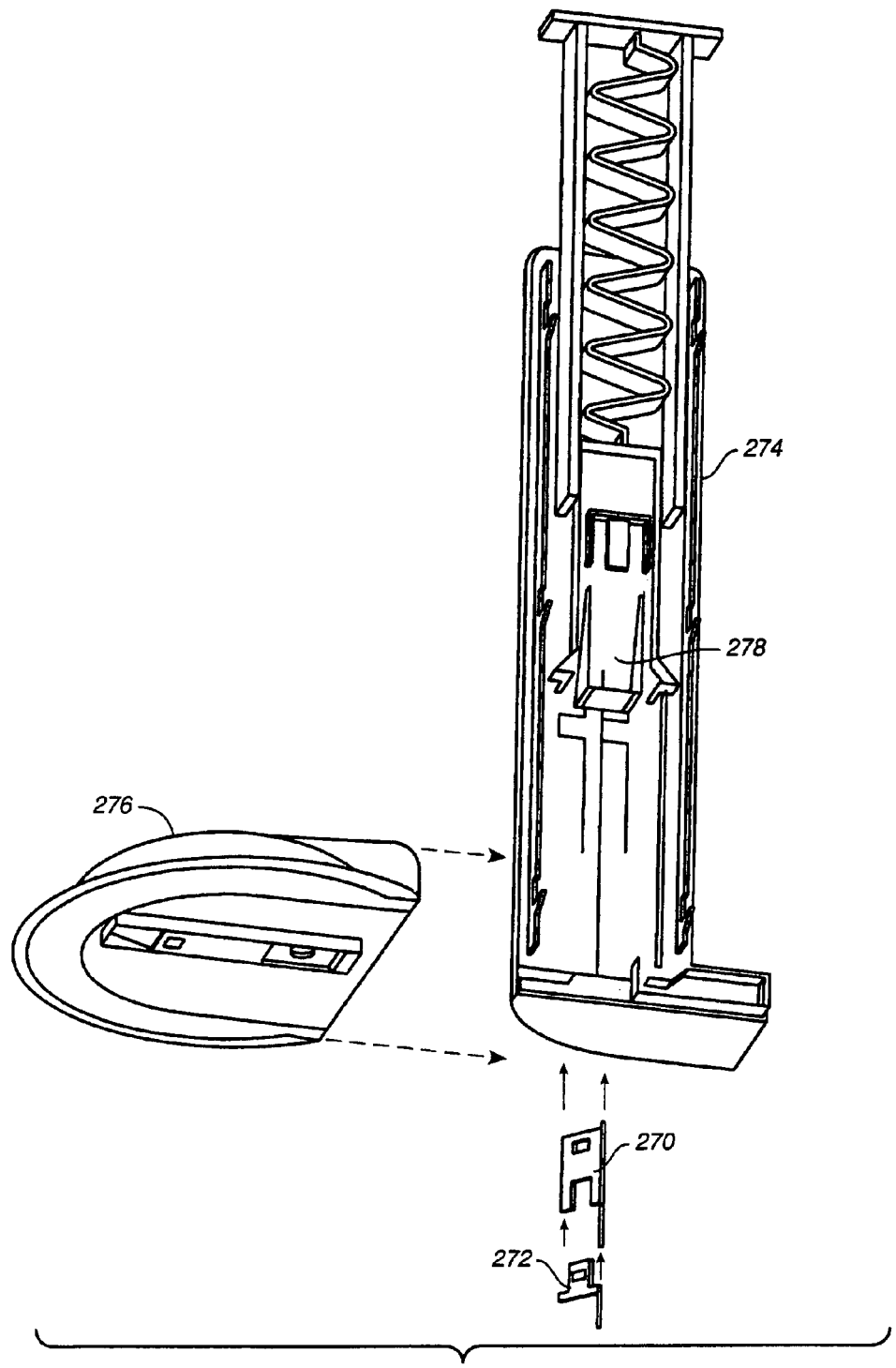
FIG._12

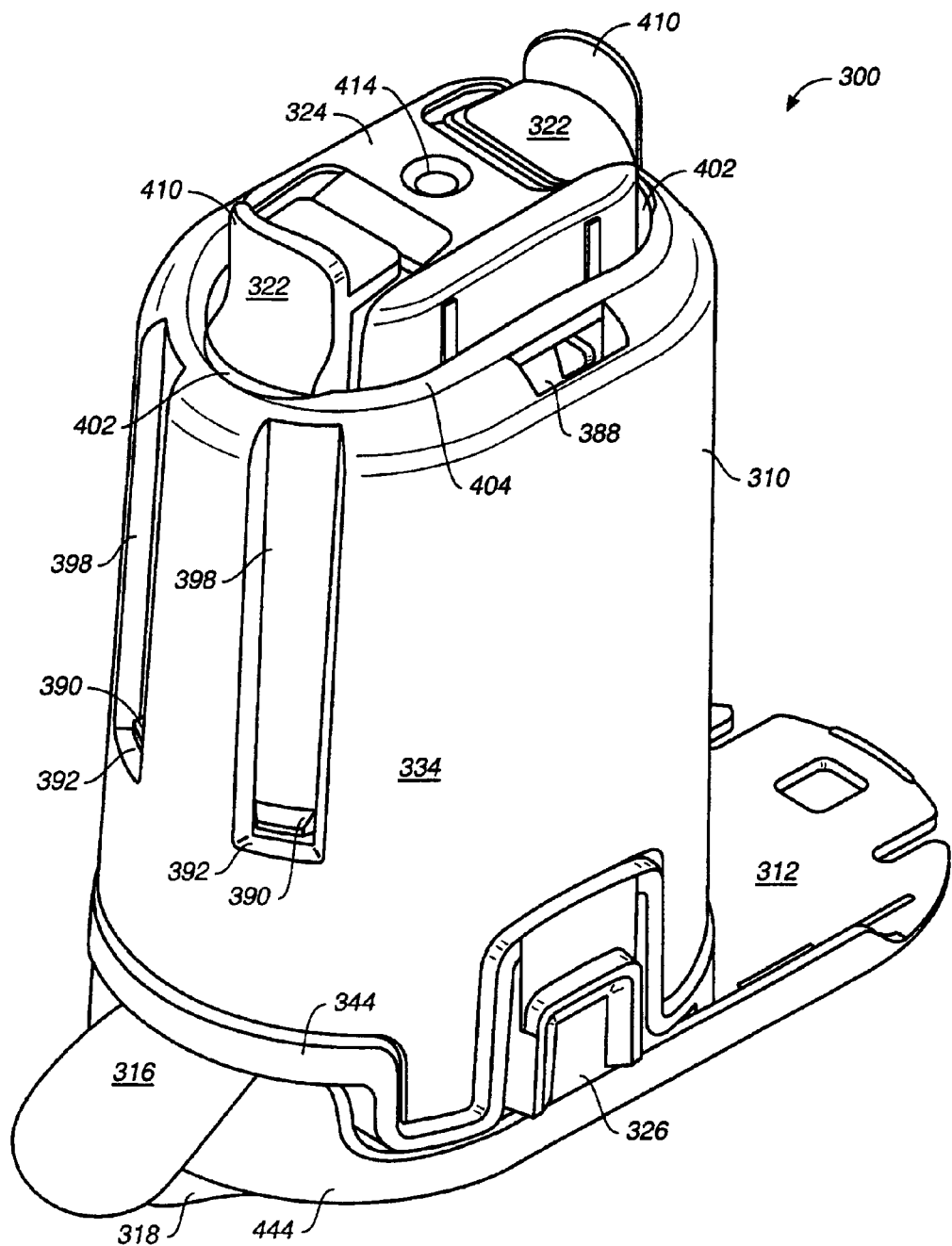
FIG._13

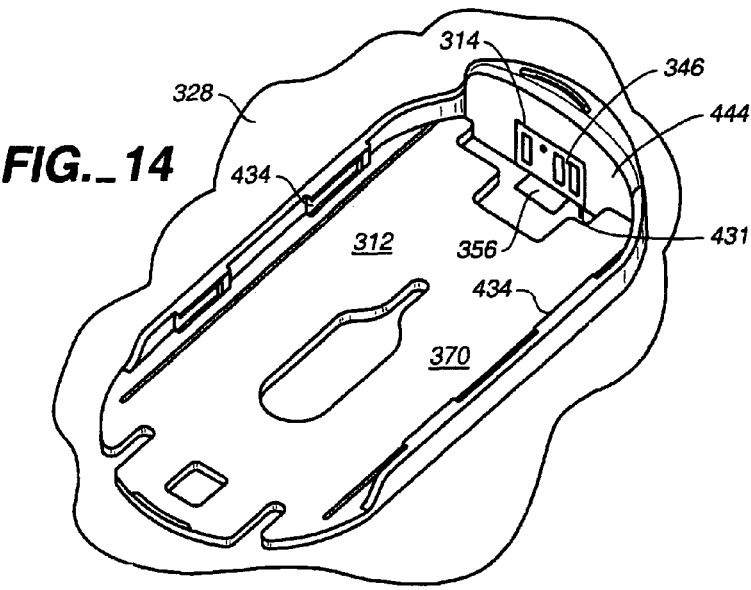
FIG._14
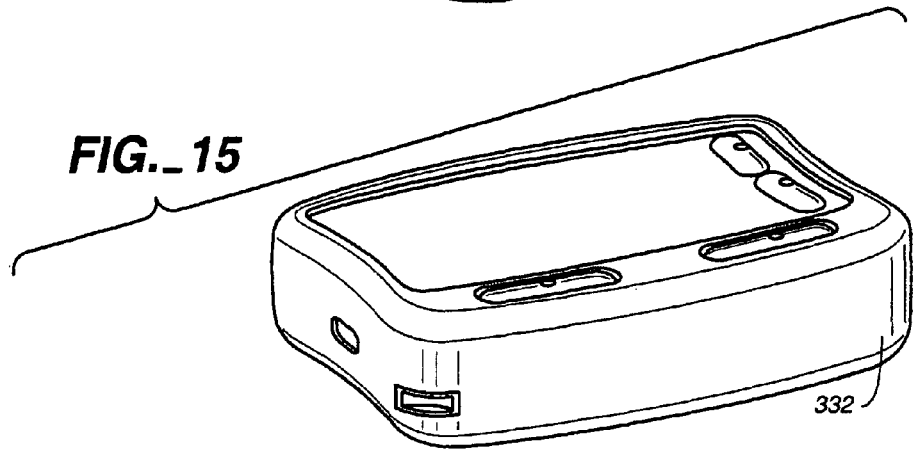
FIG._15
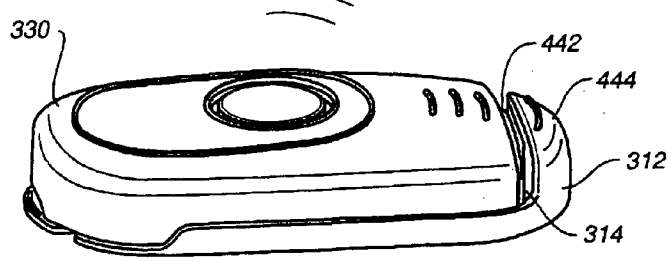

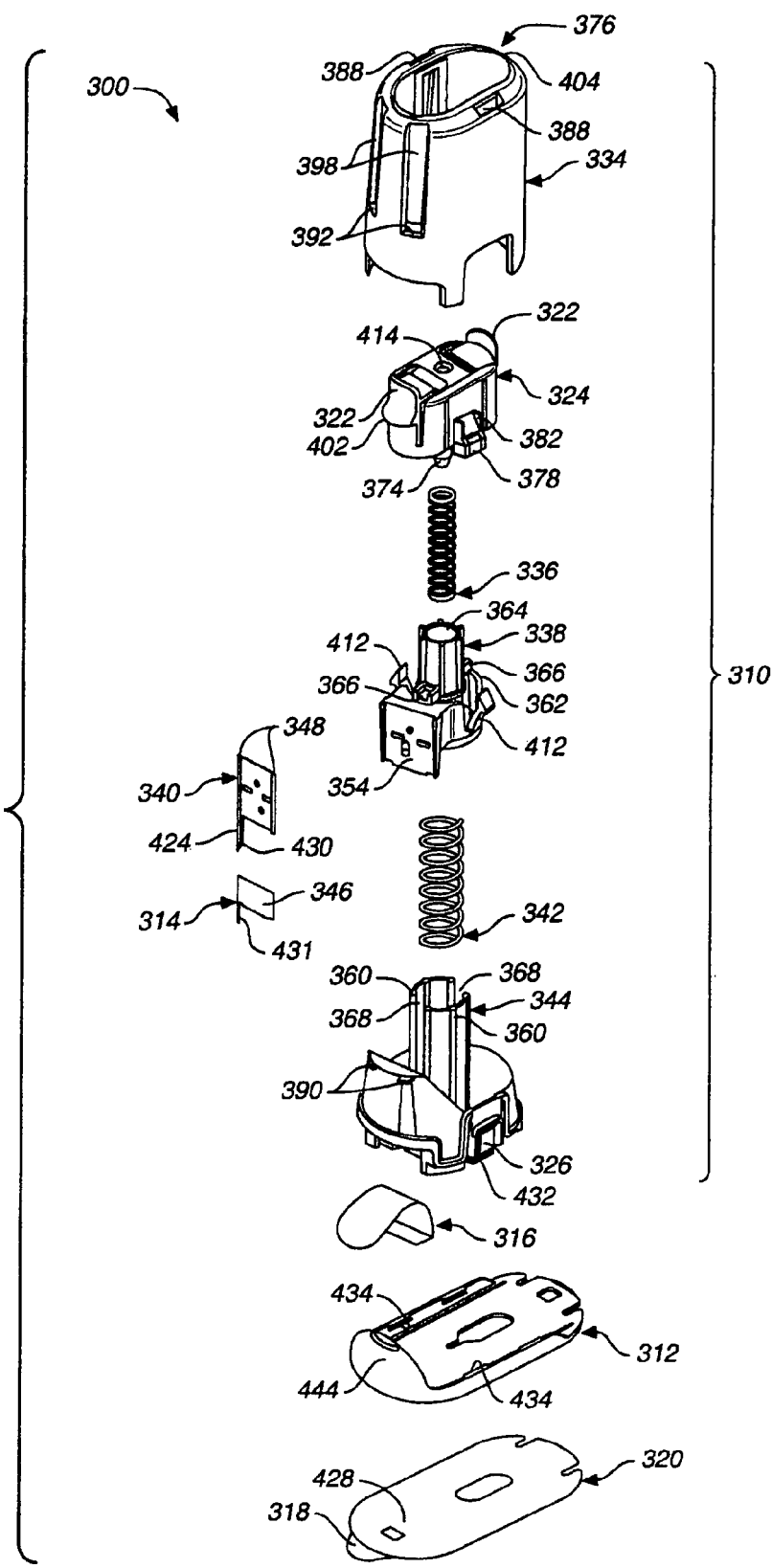
FIG._16

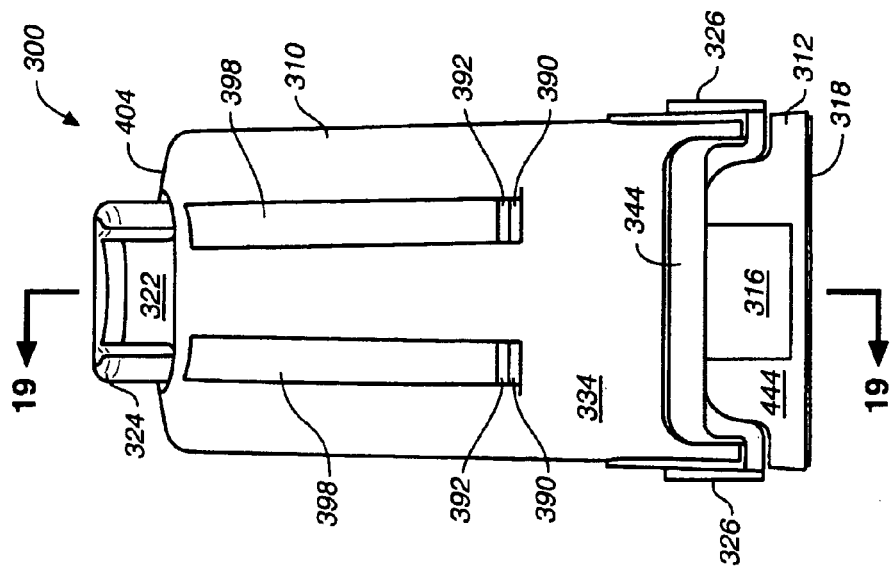
FIG._18
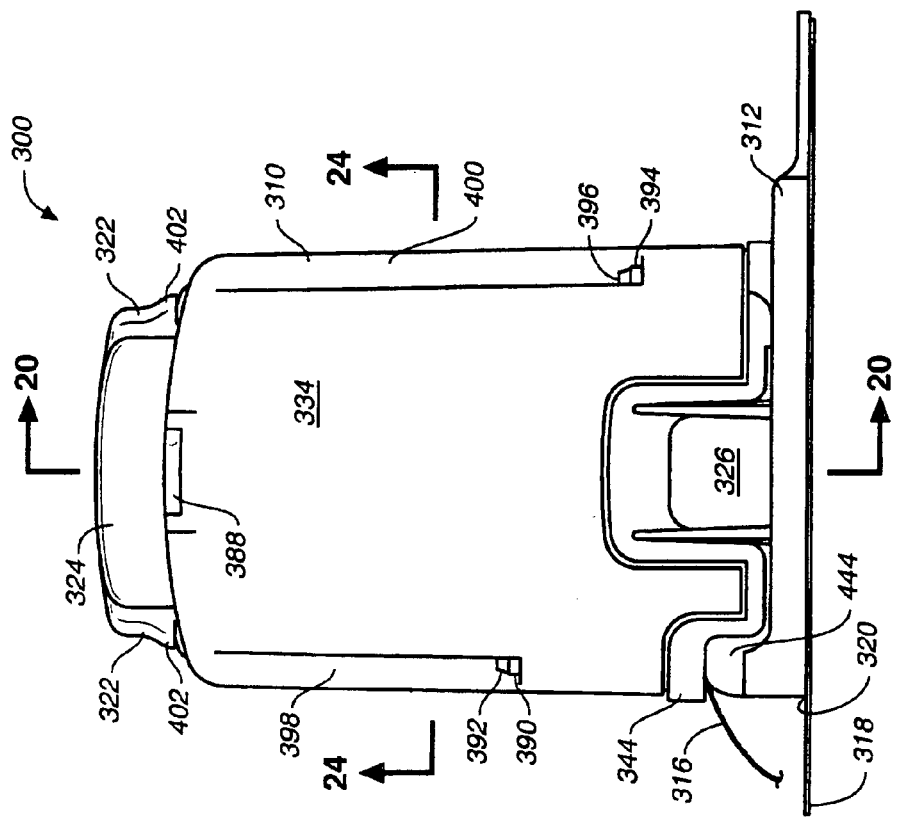
FIG._17

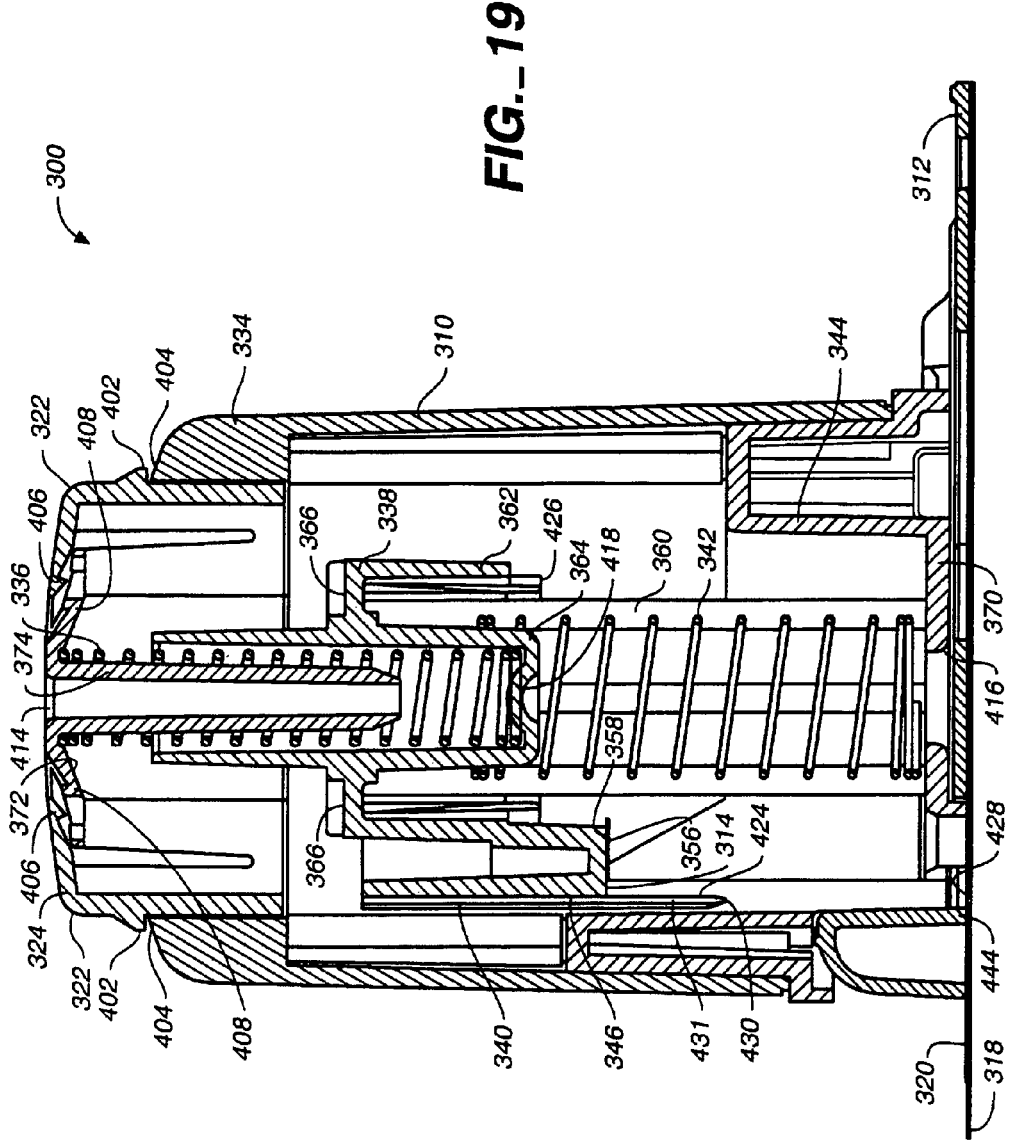
FIG._19

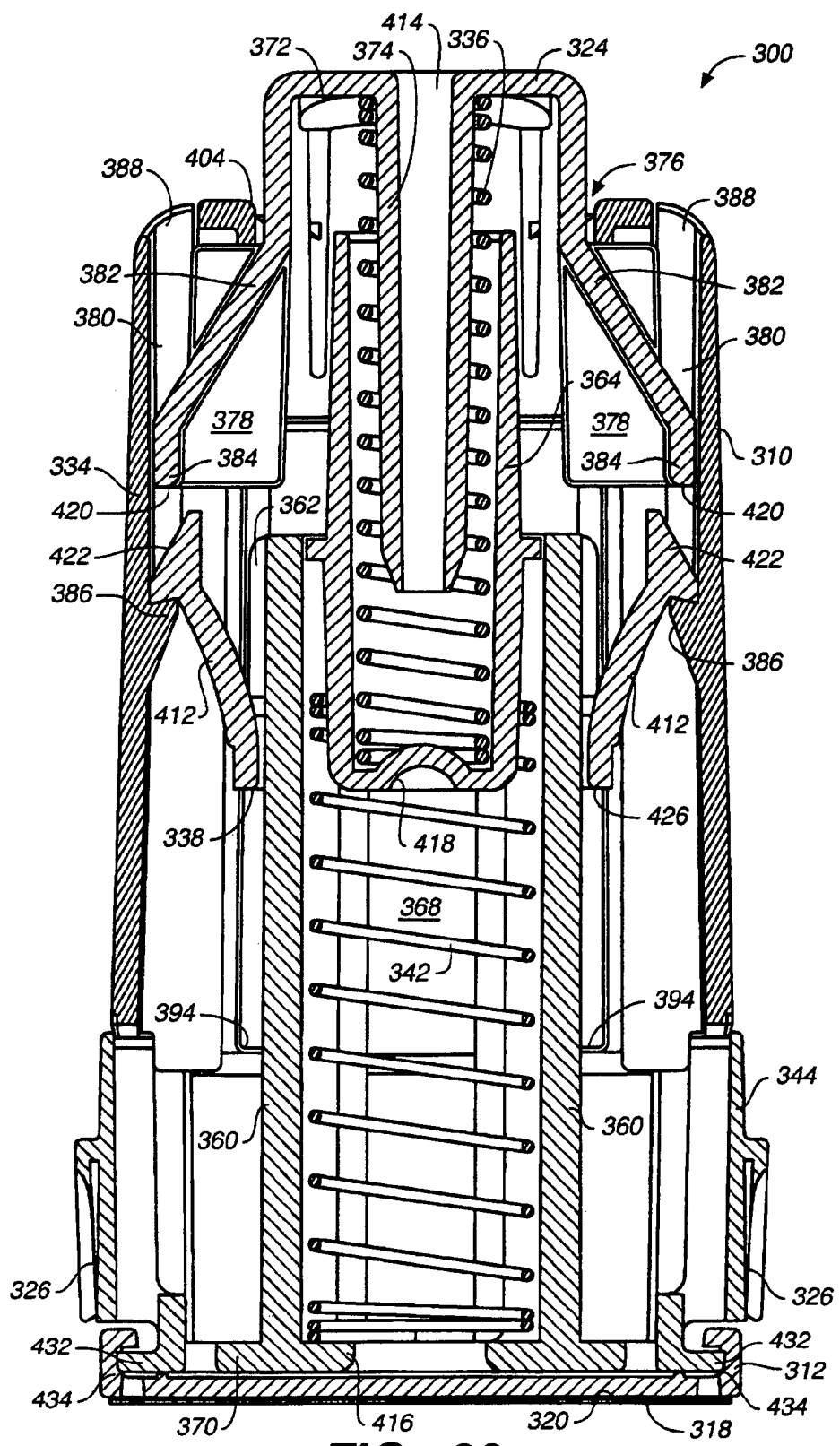
FIG._20

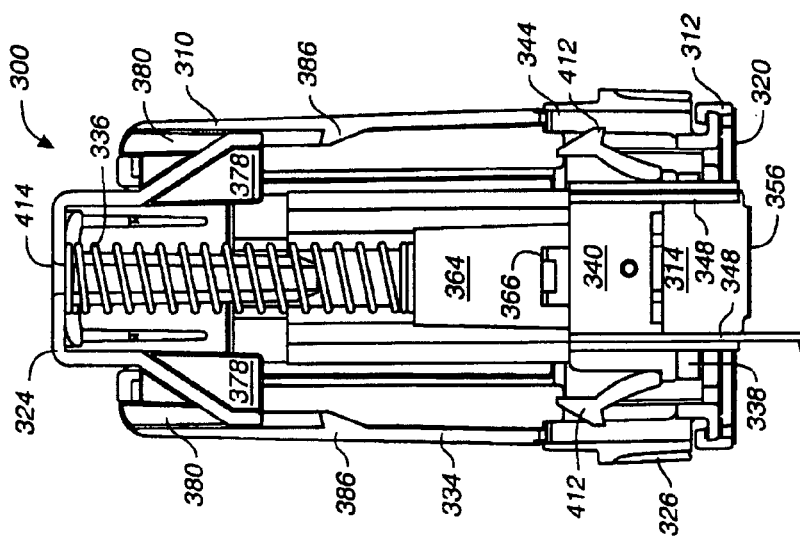
FIG._23
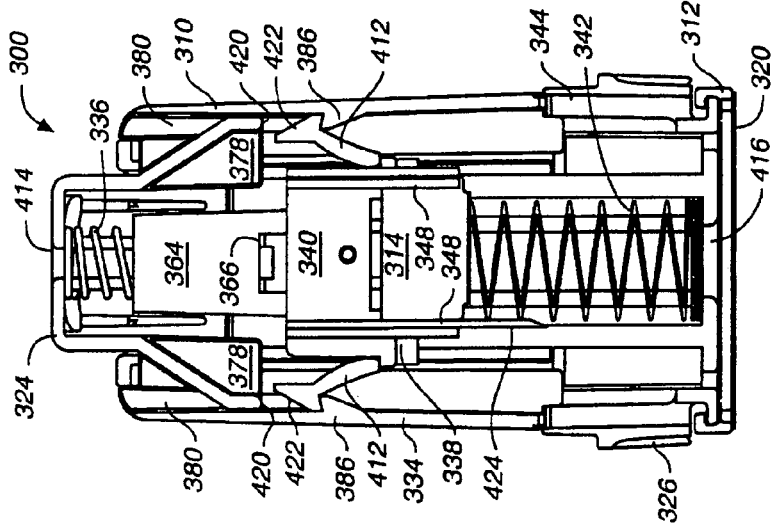
FIG._22
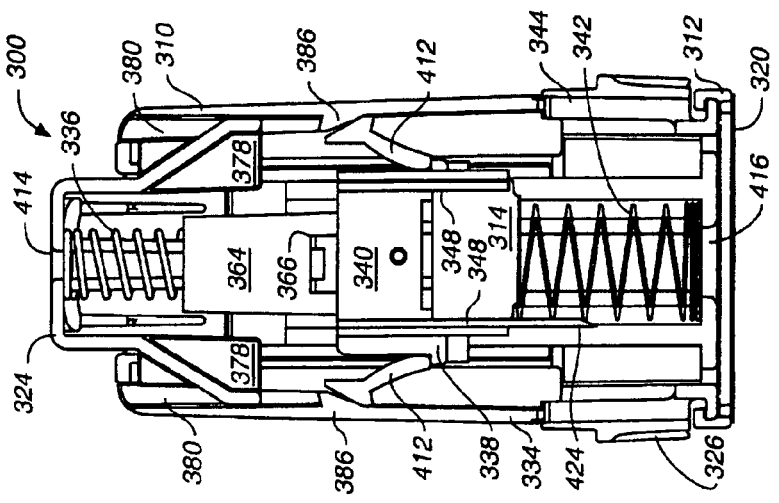
FIG._21

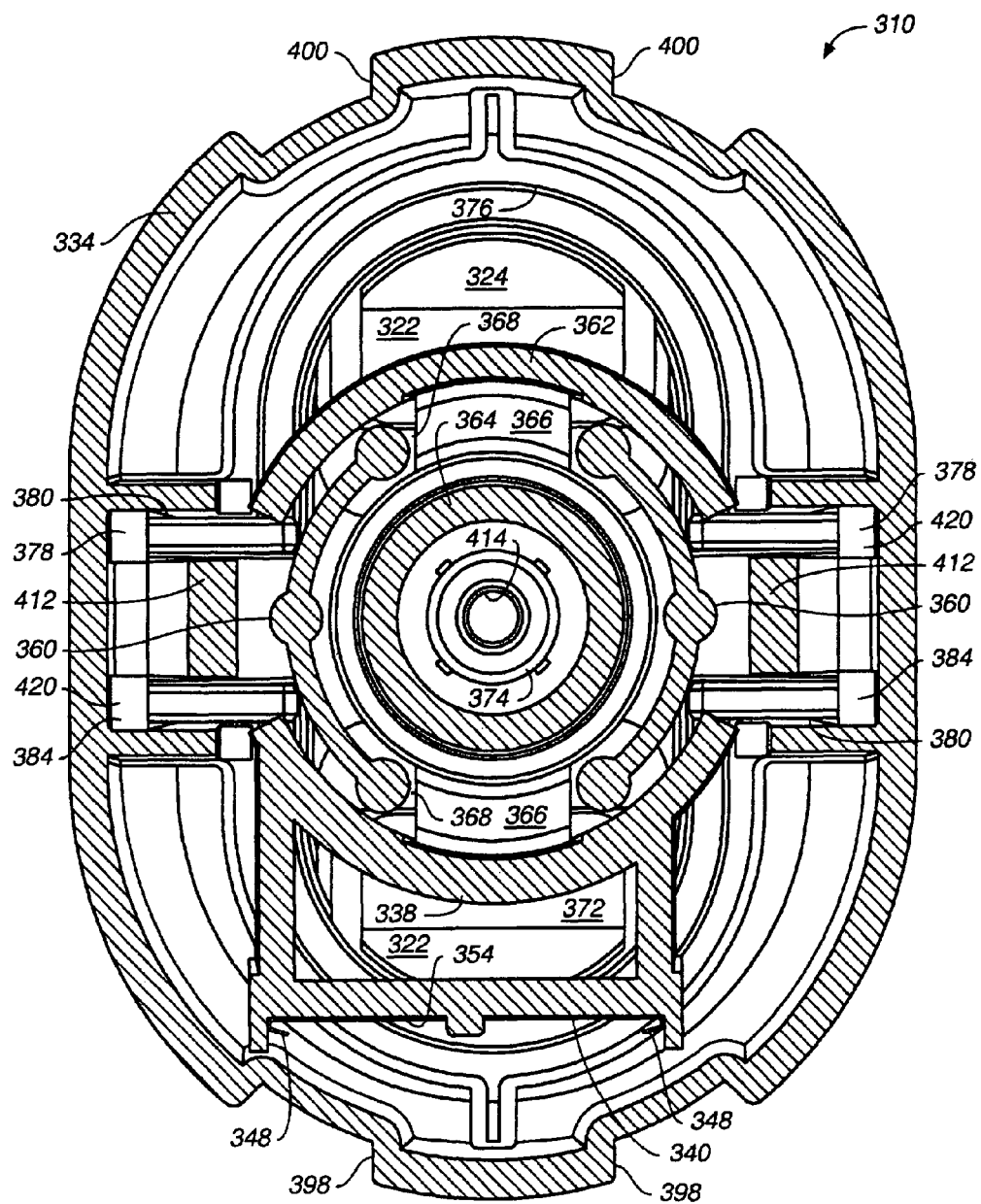
FIG._24

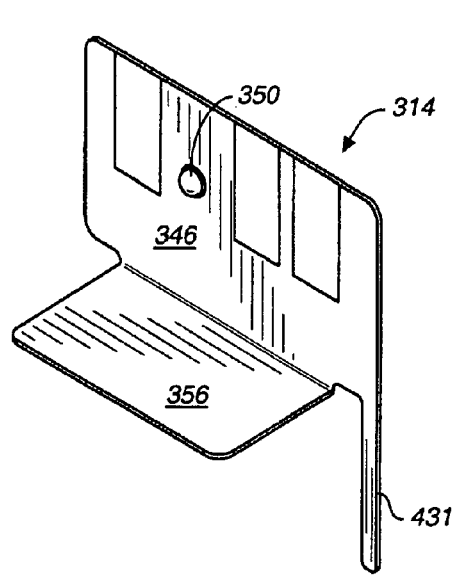
FIG._25
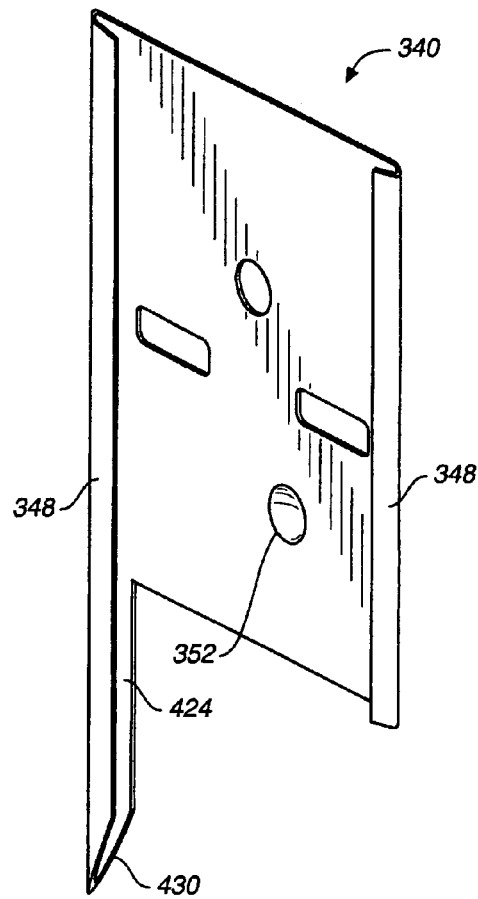
FIG._26A
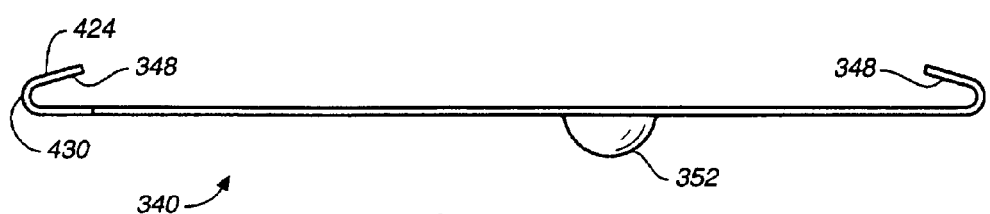
FIG._26B

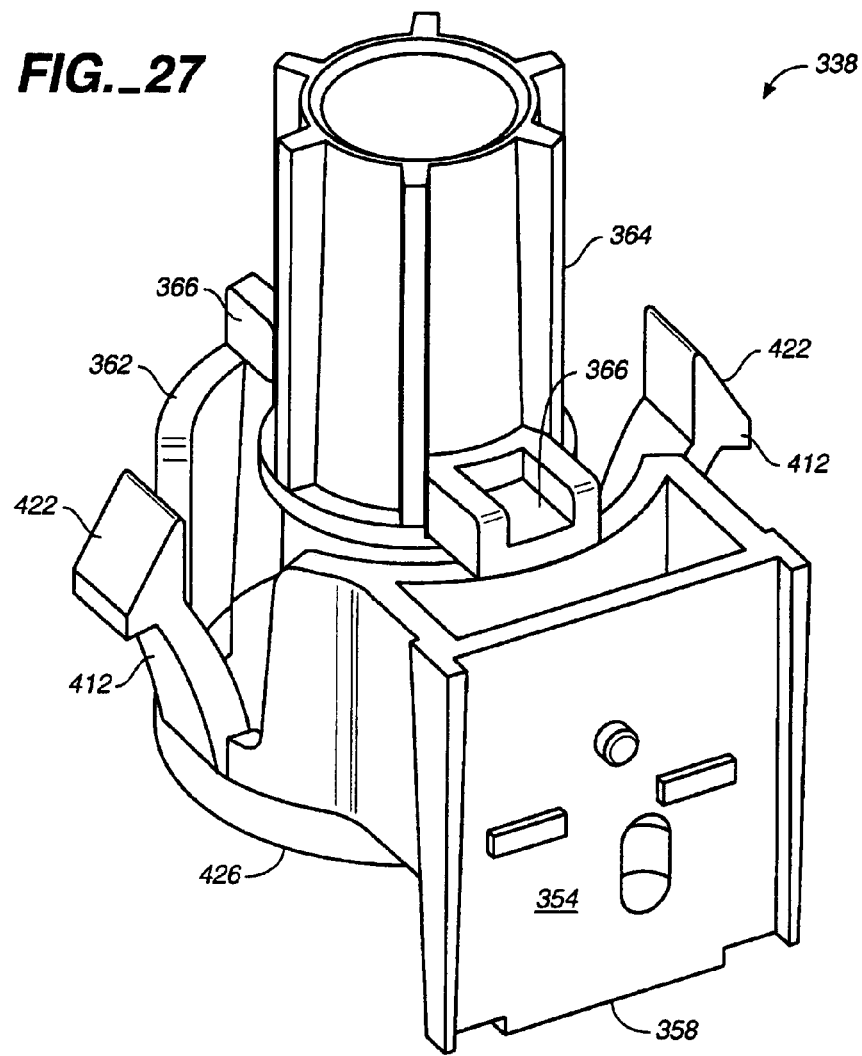
FIG._27
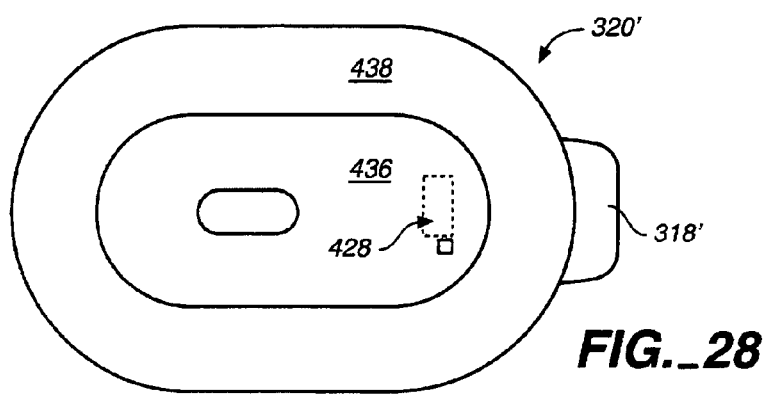
FIG._28

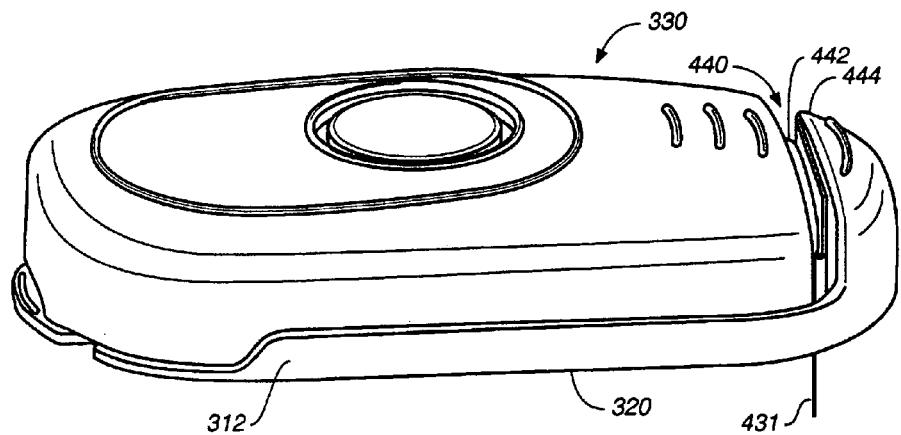
FIG._29
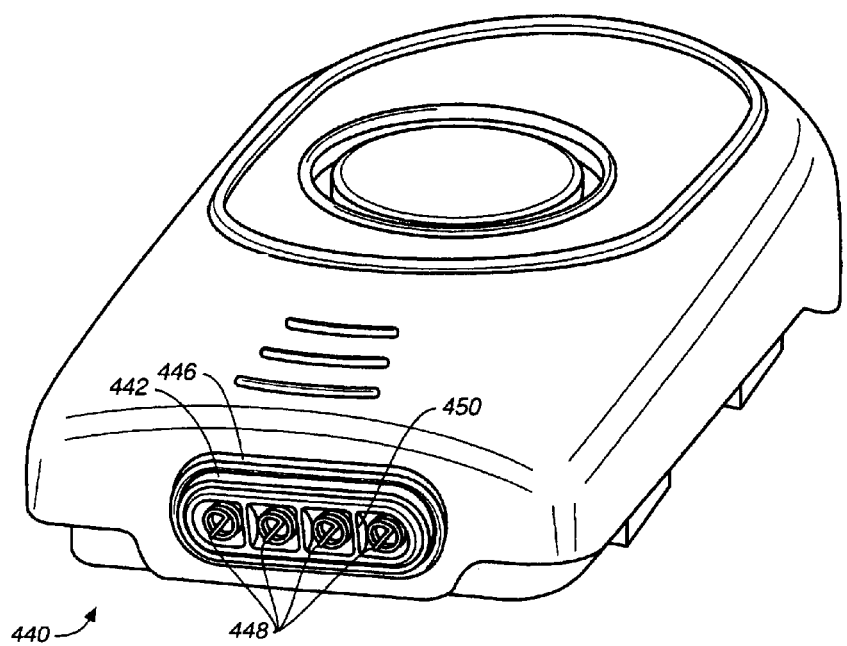
FIG._30

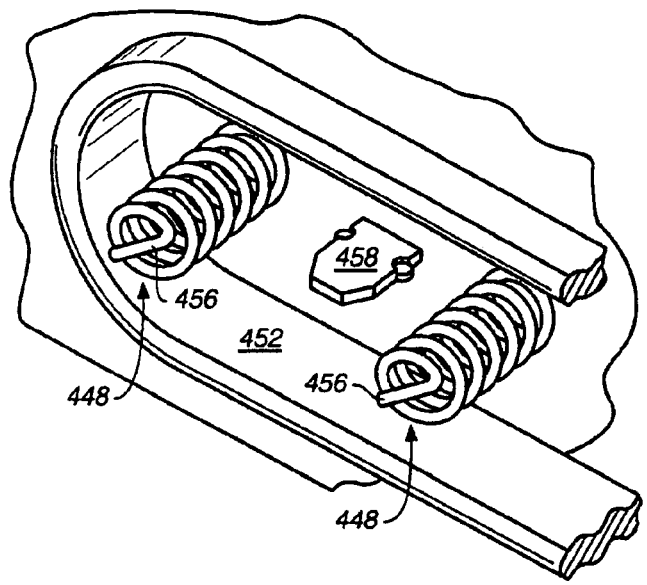
FIG._31
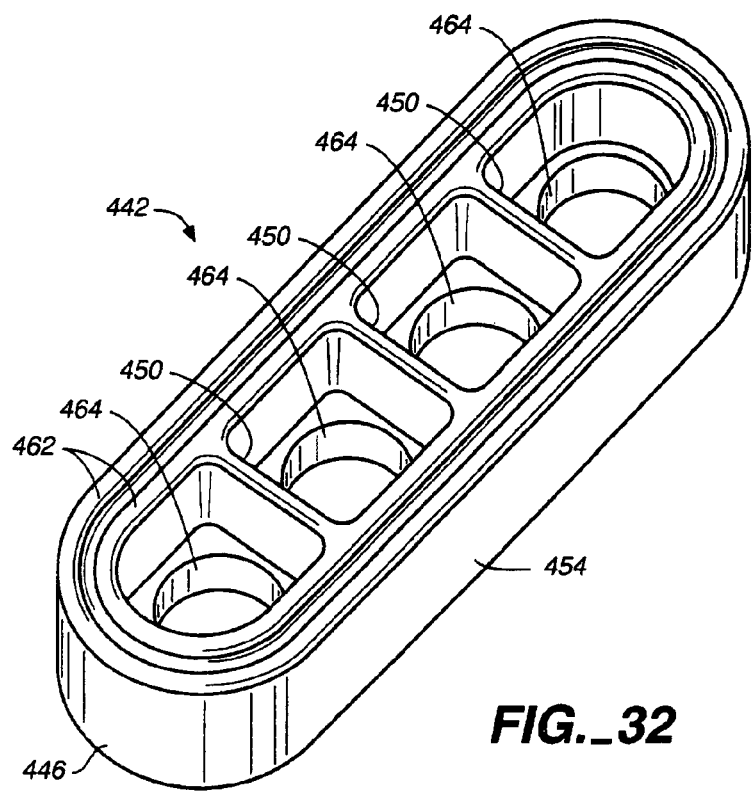
FIG._32

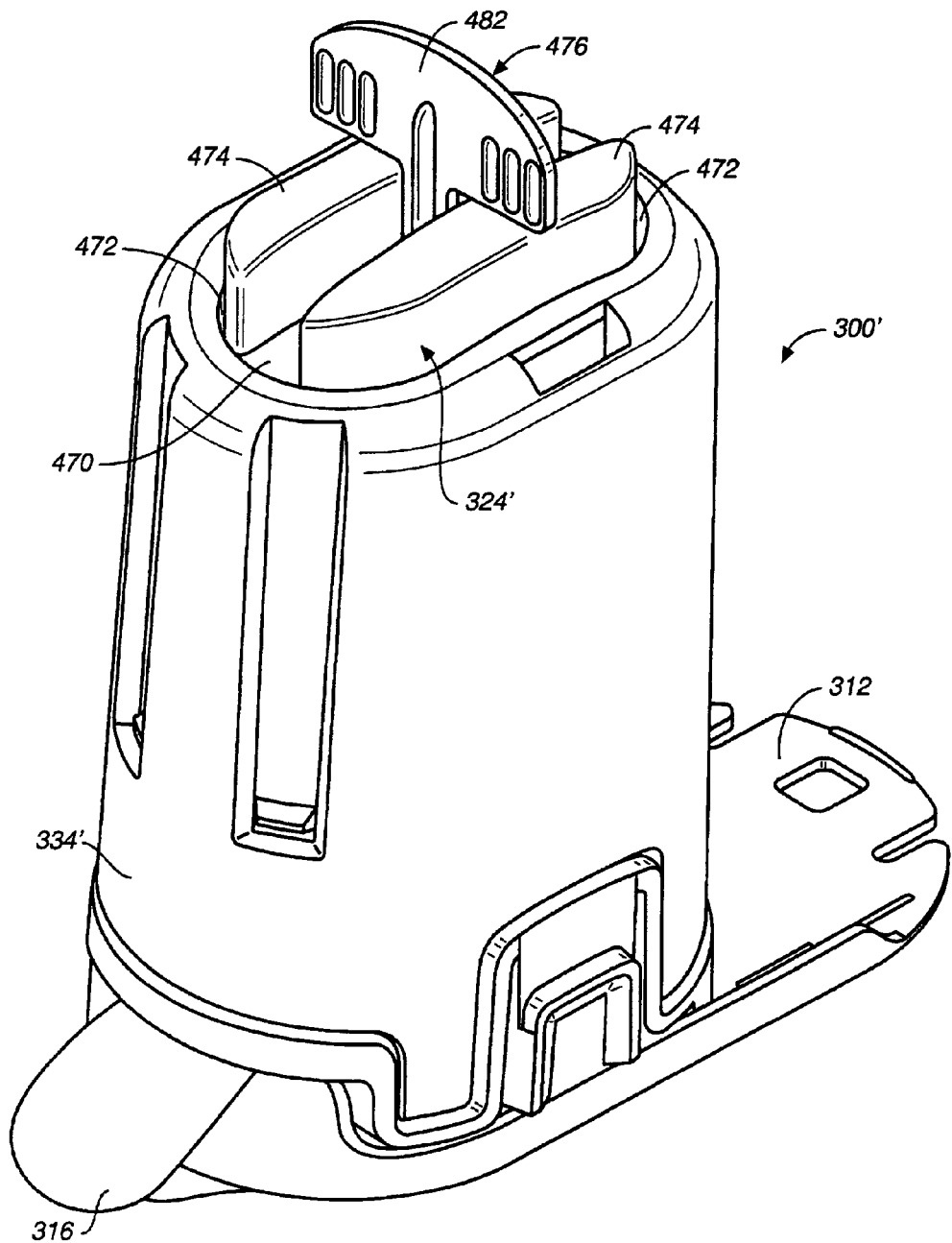
FIG._33A

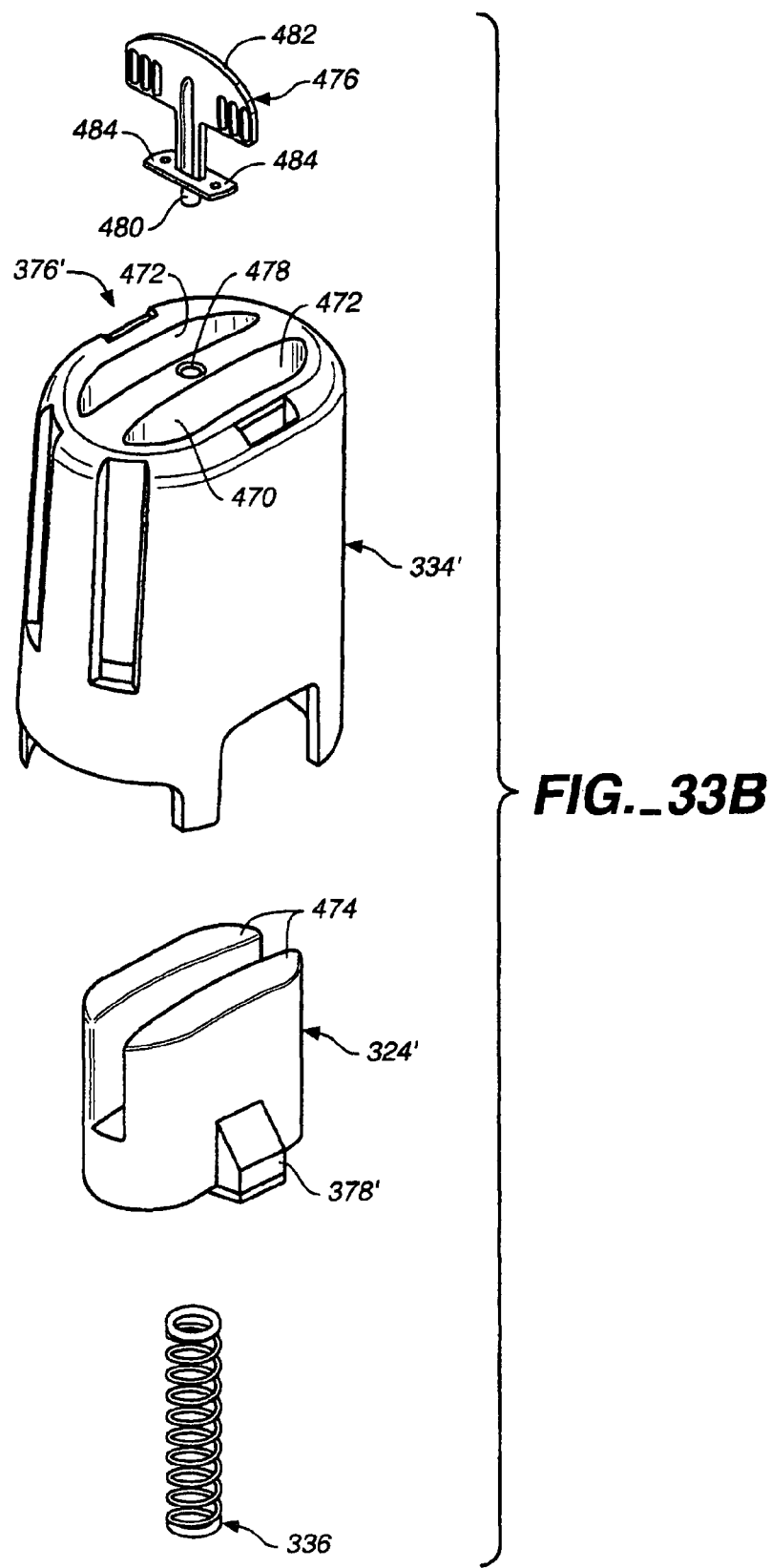
FIG._33B

SENSOR INSERTER ASSEMBLY

CROSS-REFERENCE TO RELATED APPLICATION

This application is a continuation of U.S. application Ser. No. 10/703,214, filed Nov. 5, 2003, now issued as U.S. Pat. No. 7,381,184, which claims priority to U.S. Provisional Application No. 60/424,099, entitled "Sensor Inserter Device and Methods of Use", filed Nov. 5, 2002, which is incorporated herein in its entirety by this reference.

FIELD OF THE INVENTION

The present invention is, in general, directed to devices and methods for the in vivo monitoring of an analyte, such as glucose or lactate, using a sensor to provide information to a patient about the level of the analyte. More particularly, the present invention relates to devices and methods for inserting a subcutaneously implantable electrochemical sensor in a patient for such monitoring.

BACKGROUND OF THE INVENTION

The monitoring of the level of glucose or other analytes, such as lactate or oxygen, in certain individuals is vitally important to their health. High or low levels of glucose or other analytes may have detrimental effects. The monitoring of glucose is particularly important to individuals with diabetes, as they must determine when insulin is needed to reduce glucose levels in their bodies or when additional glucose is needed to raise the level of glucose in their bodies.

A conventional technique used .by many diabetics for personally monitoring their blood glucose level includes the periodic drawing of blood, the application of that blood to a test strip, and the determination of the blood glucose level using colorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test. In addition, some individuals wish to avoid the pain associated with the test. These situations may result in hyperglycemic or hypoglycemic episodes. An in vivo glucose sensor that continuously or automatically monitors the individual's glucose level would enable individuals to more easily monitor their glucose, or other analyte, levels.

A variety of devices have been developed for continuous or automatic monitoring of analytes, such as glucose, in the blood stream or interstitial fluid. A number of these devices use electrochemical sensors which are directly implanted into a blood vessel or in the subcutaneous tissue of a patient. However, these devices are often difficult to reproducibly and inexpensively manufacture in large numbers. In addition, these devices are typically large, bulky, and/or inflexible, and many can not be used effectively outside of a controlled medical facility, such as a hospital or a doctor's office, unless the patient is restricted in his activities.

Some devices include a sensor guide which rests on or near the skin of the patient and may be attached to the patient to hold the sensor in place. These sensor guides are typically bulky and do not allow for freedom of movement. In addition, the sensor guides or the sensors include cables or wires for connecting the sensor to other equipment to direct the signals from the sensors to an analyzer. The size of the sensor guides and presence of cables and wires hinders the convenient use of these devices for everyday applications. The patient's comfort and the range of activities that can be performed while the sensor is implanted are important considerations in designing extended-use sensors for continuous or automatic in vivo monitoring of the level of an analyte, such as glucose. There is a need for a small, comfortable device which can continuously monitor the level of an analyte, such as glucose, while still permitting the patient to engage in normal activities. Continuous and/or automatic monitoring of the analyte can provide a warning to the patient when the level of the analyte is at or near a threshold level. For example, if glucose is the analyte, then the monitoring device might be configured to warn the patient of current or impending hyperglycemia or hypoglycemia. The patient can then take appropriate actions.

SUMMARY OF THE INVENTION

Generally, the present invention relates to methods and devices for the continuous and/or automatic in vivo monitoring of the level of an analyte using a subcutaneously implantable sensor. Many of these devices are small and comfortable when used, thereby allowing a wide range of activities. One embodiment includes a sensor control unit having a housing adapted for placement on skin. The housing is also adapted to receive a portion of an electrochemical sensor. The sensor control unit includes two or more conductive contacts disposed on the housing and configured for coupling to two or more contact pads on the sensor. A transmitter is disposed in the housing and coupled to the plurality of conductive contacts for transmitting data obtained using the sensor. The sensor control unit may also include a variety of optional components, such as, for example, adhesive for adhering to the skin, a mounting unit, a receiver, a processing circuit, a power supply (e.g., a battery), an alarm system, a data storage unit, a watchdog circuit, and a measurement circuit. The sensor itself has at least one working electrode and at least one contact pad coupled to the working electrode or electrodes. The sensor may also include optional components, such as, for example, a counter electrode, a counter/reference electrode, a reference electrode, and a temperature probe. The analyte monitoring system also includes a display unit that has a receiver for receiving data from the sensor control unit and a display coupled to the receiver for displaying an indication of the level of an analyte. The display unit may optionally include a variety of components, such as, for example, a transmitter, an analyzer, a data storage unit, a watchdog circuit, an input device, a power supply, a clock, a lamp, a pager, a telephone interface, a computer interface, an alarm or alarm system, a radio, and a calibration unit. In addition, the analyte monitoring system or a component of the analyte monitoring system may optionally include a processor capable of determining a drug or treatment protocol and/or a drug delivery system.

According to one aspect of the invention, an insertion kit is disclosed for inserting an electrochemical sensor into a patient. The insertion kit includes an introducer. A portion of the introducer has a sharp, rigid, planer structure adapted to support the sensor during insertion of the electrochemical sensor. The insertion kit also includes an insertion gun having a port configured to accept the electrochemical sensor and the introducer. The insertion gun has a driving mechanism for driving the introducer and electrochemical sensor into the patient, and a retraction mechanism for removing the introducer while leaving the sensor within the patient.

According to another aspect of the invention, a method of using an electrochemical sensor is disclosed. A mounting unit is adhered to skin of a patient. An insertion gun is aligned with a port on the mounting unit. The electrochemical sensor is disposed within the insertion gun and then the electrochemical sensor is inserted into the skin of the patient using the insertion gun. The insertion gun is removed and a housing of the sensor control unit is mounted on the mounting base. A plurality of conductive contacts disposed on the housing is coupled to a plurality of contact pads disposed on the electrochemical sensor to prepare the sensor for use.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a block diagram of one embodiment of a subcutaneous analyte monitor using a subcutaneously implantable analyte sensor, according to the invention.

FIG. 2 is a top view of one embodiment of an analyte sensor, according to the invention.

FIG. 3 is an expanded side view of one embodiment of a sensor and an introducer, according to the invention.

FIGS. 4A, 4B, 4C are cross-sectional views of three embodiments of the introducer of FIG. 3.

FIG. 5 is a cross-sectional view of one embodiment of a on-skin sensor control unit, according to the invention.

FIG. 6 is a top view of a base of the on-skin sensor control unit of FIG. 5.

FIG. 7 is a bottom view of a cover of the on-skin sensor control unit of FIG. 5.

FIG. 8 is a perspective view of the on-skin sensor control unit of FIG. 5 on the skin of a patient.

FIG. 9 is a perspective view of the internal structure of an insertion gun, according to the invention.

FIG. 10A is a top view of one embodiment of an on-skin sensor control unit, according to the invention.

FIG. 10B is a top view of one embodiment of a mounting unit of the on-skin sensor control unit of FIG. 10A.

FIG. 11A is a top view of another embodiment of an on-skin sensor control unit after insertion of an introducer and a sensor, according to the invention.

FIG. 11B is a top view of one embodiment of a mounting unit of the on-skin sensor control unit of FIG. 11A.

FIG. 11C is a top view of one embodiment of a housing for at least a portion of the electronics of the on-skin sensor control unit of FIG. 11A.

FIG. 11D is a bottom view of the housing of FIG. 11C.

FIG. 11E is a top view of the on-skin sensor control unit of FIG. 11A with a cover of the housing removed.

FIG. 12 depicts an introducer, sensor, insertion gun and mounting unit, which can be assembled and sold together in an insertion kit.

FIG. 13 is a perspective view showing a preferred commercial embodiment of a sensor inserter and adhesive mount constructed according to the invention.

FIG. 14 is a perspective view of the adhesive mount and sensor attached to the patient's skin.

FIG. 15 is a perspective view of the transmitter attached to the adhesive mount.

FIG. 16 is an exploded perspective view of the preferred commercial embodiment of FIG. 13.

FIG. 17 is a side elevation view of the preferred commercial embodiment of FIG. 13.

FIG. 18 is an end elevation view of the preferred commercial embodiment of FIG. 13.

FIG. 19 is a cross-sectional view taken along line 19-19 in FIG. 18.

FIG. 20 is a cross-sectional view taken along line 20-20 in FIG. 17.

FIG. 21 is a broken away view similar to FIG. 20, showing the shuttle in the neutral position.

FIG. 22 is a broken away view similar to FIG. 20, showing the shuttle in the cocked position.

FIG. 23 is a broken away view similar to FIG. 20, showing the shuttle in the insertion position.

FIG. 24 is a cross-sectional view taken along line 24-24 in FIG. 17.

FIG. 25 is a perspective view of a transcutaneously implantable sensor.

FIG. 26A is a perspective view of a sensor introducer.

FIG. 26B is a bottom view of the introducer shown in FIG. 26A.

FIG. 27 is a perspective view of a shuttle member.

FIG. 28 is a top plan view of an oversized adhesive tape.

FIG. 29 is a perspective view of the transmitter attached to the adhesive mount and showing the sensor sandwiched therebetween.

FIG. 30 is a perspective view of the interconnect on one end of the transmitter.

FIG. 31 is an enlarged perspective view of the interconnect of FIG. 30 with the seal and one spring removed for clarity.

FIG. 32 is an enlarged perspective view of the interconnect seal.

FIG. 33A is a perspective view of an alternative embodiment of a sensor inserter kit.

FIG. 33B is an exploded view of some of the components shown assembled in FIG. 33A.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The present invention is applicable to an analyte monitoring system using an implantable sensor for the in vivo determination of a concentration of an analyte, such as glucose or lactate, in a fluid. The sensor can be, for example, subcutaneously implanted in a patient for the continuous or periodic monitoring an analyte in a patient's interstitial fluid. This can then be used to infer the glucose level in the patient's bloodstream. Other in vivo analyte sensors can be made, according to the invention, for insertion into a vein, artery, or other portion of the body containing fluid. The analyte monitoring system is typically configured for monitoring the level of the analyte over a time period which may range from days to weeks or longer.

The analyte monitoring systems of the present invention can be utilized under a variety of conditions. The particular configuration of a sensor and other units used in the analyte monitoring system may depend on the use for which the analyte monitoring system is intended and the conditions under which the analyte monitoring system will operate. One embodiment of the analyte monitoring system includes a sensor configured for implantation into a patient or user. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels, in blood or other fluids. The site and depth of implantation may affect the particular shape, components, and configuration of the sensor. Subcutaneous implantation may be preferred, in some cases, to limit the depth of implantation of the sensor. Sensors may also be implanted in other regions of the body to determine analyte levels in other fluids. Examples of suitable sensor for use in the analyte monitoring systems of the invention are described in U.S. patent applications, Ser. No. 09/034,372, issued as U.S. Pat. No. 6,134,461 on Oct. 17, 2000, and Ser. No. 09/753,746, issued as U.S. Pat. No. 6,560,471 on May 6, 2003, both incorporated herein by reference.

One embodiment of the analyte monitoring system 40 for use with an implantable sensor 42, and particularly for use with a subcutaneously implantable sensor, is illustrated in block diagram form in FIG. 1. The analyte monitoring system 40 includes, at minimum, a sensor 42, a portion of which is configured for implantation (e.g., subcutaneous, venous, or arterial implantation) into a patient, and a sensor control unit 44. The sensor 42 is coupled to the sensor control unit 44 which is typically attached to the skin of a patient. The sensor control unit 44 operates the sensor 42, including, for example, providing a voltage across the electrodes of the sensor 42 and collecting signals from the sensor 42. The sensor control unit 44 may evaluate the signals from the sensor 42 and/or transmit the signals to one or more optional receiver/display units 46, 48 for evaluation. The sensor control unit 44 and/or the receiver/display units 46, 48 may display or otherwise communicate the current level of the analyte. Furthermore, the sensor control unit 44 and/or the receiver/display units 46, 48 may indicate to the patient, via, for example, an audible, visual, or other sensory-stimulating alarm, when the level of the analyte is at or near a threshold level. In some embodiments, a electrical shock can be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

A sensor 42 includes at least one working electrode 58 formed on a substrate 50, as shown in FIG. 2. The sensor 42 may also include at least one counter electrode 60 (or counter/reference electrode) and/or at least one reference electrode 62. The substrate 50 of the sensor may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In some embodiments, the substrate is flexible. For example, if the sensor 42 is configured for implantation into a patient, then the sensor 42 may be made flexible (although rigid sensors may also be used for implantable sensors) to reduce pain to the patient and damage to the tissue caused by the implantation of and/or the wearing of the sensor 42. A flexible substrate 50 often increases the patient's comfort and allows a wider range of activities. Suitable materials for a flexible substrate 50 include, for example, non-conducting plastic or polymeric materials and other non-conducting, flexible, deformable materials. Examples of useful plastic. or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors 42 are made using a relatively rigid substrate 50 to, for example, provide structural support against bending or breaking. Examples of rigid materials that may be used as the substrate 50 include poorly conducting ceramics, such as aluminum oxide and silicon dioxide. One advantage of an implantable sensor 42 having a rigid substrate is that the sensor 42 may have a sharp point and/or a sharp edge to aid in implantation of a sensor 42 without an additional introducer.

It will be appreciated that for many sensors 42 and sensor applications, both rigid and flexible sensors will operate adequately. The flexibility of the sensor 42 may also be controlled and varied along a continuum by changing, for example, the composition and/or thickness of the substrate 50.

In addition to considerations regarding flexibility, it is often desirable that implantable sensors 42 should have a substrate 50 which is non-toxic. Preferably, the substrate 50 is approved by one or more appropriate governmental agencies or private groups for in vivo use.

Although the substrate 50 in at least some embodiments has uniform dimensions along the entire length of the sensor 42, in other embodiments, the substrate 50 has a distal end 67 and a proximal end 65 with different widths 53, 55, respectively, as illustrated in FIG. 2. In these embodiments, the distal end 67 of the substrate 50 may have a relatively narrow width 53. For sensors 42 which are implantable into the subcutaneous tissue or another portion of a patient's body, the narrow width 53 of the distal end 67 of the substrate 50 may facilitate the implantation of the sensor 42. Often, the narrower the width of the sensor 42, the less pain the patient will feel during implantation of the sensor and afterwards. The sensor 42 is designed to be a replaceable component in an implantable analyte monitor. Typically, the sensor 42 is capable of operation over a period of days. Preferably, the period of operation is at least three days. The sensor 42 can then be removed and replaced with a new sensor.

An introducer 120 can be used to subcutaneously insert the sensor 42 into the patient, as illustrated in FIG. 3. The introducer 120 is typically formed using structurally rigid materials, such as metal or rigid plastic. Preferred materials include stainless steel and ABS (acrylonitrile-butadiene-styrene) plastic. In some embodiments, the introducer 120 is pointed and/or sharp at the tip 121 to facilitate penetration of the skin of the patient. A sharp, thin introducer may reduce pain felt by the patient upon insertion of the sensor 42. In other embodiments, the tip 121 of the introducer 120 has other shapes, including a blunt or flat shape. These embodiments may be particularly useful when the introducer 120 does not penetrate the skin but rather serves as a structural support for the sensor 42 as the sensor 42 is pushed into the skin.

The introducer 120 may have a variety of cross-sectional shapes, as shown in FIGS. 4A, 4B, and 4C. The introducer 120 illustrated in FIG. 4A is a flat, planar, pointed strip of rigid material which may be attached or otherwise coupled to the sensor 42 to ease insertion of the sensor 42 into the skin of the patient, as well as to provide structural support to the sensor 42 during insertion. The introducers 120 of FIGS. 4B and 4C are U- or V-shaped implements that support the sensor 42 to limit the amount that the sensor 42 may bend or bow during insertion. The cross-sectional width 124 of the introducers 120 illustrated in FIGS. 4B and 4C is typically 1 mm or less, preferably 700 μm or less, more preferably 500 μm or less, and most preferably. 300 μm or less. The cross-sectional height 126 of the introducer 120 illustrated in FIGS. 4B and 4C is typically about 1 mm or less, preferably about 700 μm or less, and more preferably about 500 μm or less.

The sensor 42 itself may include optional features to facilitate insertion. For example, the sensor 42 may be, pointed at the tip 123 to ease insertion, as illustrated in FIG. 3. In addition, the sensor 42 may include a barb 125 which helps retain the sensor 42 in the subcutaneous tissue of the patient. The barb 125 may also assist in anchoring the sensor 42 within the subcutaneous tissue of the patient during operation of the sensor 42. However, the barb 125 is typically small enough that little damage is caused to the subcutaneous tissue when the sensor 42 is removed for replacement. The sensor 42 may also include a notch 127 that can be used in cooperation with a corresponding structure (not shown) in the introducer to apply pressure against the sensor 42 during insertion, but disengage as the introducer 120 is removed. One example of such a structure in the insertion device is a rod (not shown) between two opposing sides of an introducer 120 and at an appropriate height of the introducer 120.

In operation, the sensor 42 is placed within or next to the introducer 120 and then a force is provided against the introducer 120 and/or sensor 42 to carry the sensor 42 into the skin of the patient. In one embodiment, the force is applied to the sensor 42 to push the sensor into the skin, while the introducer 120 remains stationary and provides structural support to the sensor 42. Alternatively, the force is applied to the introducer 120 and optionally to the sensor 42 to push a portion of both the sensor 42 and the introducer 120 through the ski of the patient and into the subcutaneous tissue. The introducer 120 is optionally pulled out of the skin and subcutaneous tissue with the sensor 42 remaining in the subcutaneous tissue due to frictional forces between the sensor 42 and the patient's tissue. If the sensor 42 includes the optional barb 125, then this structure may also facilitate the retention of the sensor 42 within the interstitial tissue as the barb catches in the tissue.

The force applied to the introducer 120 and/or the sensor 42 may be applied manually or mechanically. Preferably, the sensor 42 is reproducibly inserted through the skin of the patient. In one embodiment, an insertion gun is used to insert the sensor. One example of an insertion gun 200 for inserting a sensor 42 is shown in FIG. 9. The insertion gun 200 includes a housing 202 and a carrier 204. The introducer 120 is typically mounted on the carrier 204 and the sensor 42 is preloaded into the introducer 120. The carrier 204 drives the sensor 42 and, optionally, the introducer 120 into the skin of the patient using, for example, a cocked or wound spring, a burst of compressed gas, an electromagnet repelled by a second magnet, or the like, within the insertion gun 200. In some instances, for example, when using a spring, the carrier 204 and introducer 120 may be moved, cocked, or otherwise prepared to be directed towards the skin of the patient.

After the sensor 42 is inserted, the insertion gun 200 may contain a mechanism which pulls the introducer 120 out of the skin of the patient. Such a mechanism may use a spring, electromagnet, or the like to remove the introducer 120.

The insertion gun may be reusable. The introducer 120 is often disposable to avoid the possibility of contamination. Alternatively, the introducer 120 may be sterilized and reused. In addition, the introducer 120 and/or the sensor 42 may be coated with an anticlotting agent to prevent fouling of the sensor 42.

In one embodiment, the sensor 42 is injected between 2 to 12 mm into the interstitial tissue of the patient for subcutaneous implantation. Preferably, the sensor is injected 3 to 9 mm, and more preferably 5 to 7 mm, into the interstitial tissue. Other embodiments of the invention, may include sensors implanted in other portions of the patient, including, for example, in an artery, vein, or organ. The depth of implantation varies depending on the desired implantation target.

Although the sensor 42 may be inserted anywhere in the body, it is often desirable that the insertion site be positioned so that the on-skin sensor control unit 44 can be concealed. In addition, it is often desirable that the insertion site be at a place on the body with a low density of nerve endings to reduce the pain to the patient. Examples of preferred sites for insertion of the sensor 42 and positioning of the on-skin sensor control unit 44 include the abdomen, thigh, leg, upper arm, and shoulder.

An insertion angle is measured from the plane of the skin (i.e., inserting the sensor perpendicular to the skin would be a 90° insertion angle). Insertion angles usually range from 10 to 90°, typically from 15 to 60°, and often from 30 to 45°.

On-skin Sensor Control Unit

The on-skin sensor control unit 44 is configured to be placed on the skin of a patient. The on-skin sensor control unit 44 is optionally formed in a shape that is comfortable to the patient and which may permit concealment, for example, under a patient's clothing. The thigh, leg, upper arm, shoulder, or abdomen are convenient parts of the patient's body for placement of the on-skin sensor control unit 44 to maintain concealment. However, the on-skin sensor control unit 44 may be positioned on other portions of the patient's body. One embodiment of the on-skin sensor control unit 44 has a thin, oval shape to enhance concealment, as illustrated in FIGS. 5-7. However, other shapes and sizes may be used.

The particular profile, as well as the height, width, length, weight, and volume of the on-skin sensor control unit 44 may vary and depends, at least in part, on the components and associated functions included in the on-skin sensor control unit 44, as discussed below. For example, in some embodiments, the on-skin sensor control unit 44 has a height of 1.3 cm or less, and preferably 0.7 cm or less. In some embodiments, the on-skin sensor control unit 44 has a weight of 90 grams or less, preferably 45 grams or less, and more preferably 25 grams or less. In some embodiments, the on-skin sensor control unit 44 has a volume of about 15 $cm^3$ or less, preferably about 10 $cm^3$ or less, more preferably about 5 $cm^3$ or less, and most preferably about 2.5 $cm^3$ or less.

The on-skin sensor control unit 44 includes a housing 45, as illustrated in FIGS. 5-7. The housing 45 is typically formed as a single integral unit that rests on the skin of the patient. The housing 45 typically contains most or all of the electronic components, described below, of the on-skin sensor control unit 44. The on-skin sensor control, unit 44 usually includes no additional cables or wires to other electronic components or other devices. If the housing includes two or more parts, then those parts typically fit together to form a single integral unit.

In some embodiments, conductive contacts 80 are provided on the exterior of the housing 45. In other embodiments, the conductive contacts 80 are provided on the interior of the housing 45, for example, within a hollow or recessed region.

In some embodiments, the housing 45 of the on-skin sensor control unit 44 is a single piece. The conductive contacts 80 may be formed on the exterior of the housing 45 or on the interior of the housing 45 provided there is a port 78 in the housing 45 through which the sensor 42 can be directed to access the conductive contacts 80.

In other embodiments, the housing 45 of the on-skin sensor control unit 44 is formed in at least two separate portions that fit together to form the housing 45, for example, a base 74 and a cover 76, as illustrated in FIGS. 5-7. The two or more portions of the housing 45 may be entirely separate from each other. Alternatively, at least some of the two or more portions of the housing 45 may be connected together, for example, by a hinge, to facilitate the coupling of the portions to form the housing 45 of the on-skin sensor control unit 44.

These two or more separate portions of the housing 45 of the on-skin sensor control unit 44 may have complementary, interlocking structures, such as, for example, interlocking ridges or a ridge on one component and a complementary groove on another component, so that the two or more separate components may be easily and/or firmly coupled together. This may be useful, particularly if the components are taken apart and fit together occasionally, for example, when a battery or sensor 42 is replaced. However, other fasteners may also be used to couple the two or more components together, including, for example, screws, nuts and bolts, nails, staples, rivets, or the like. In addition, adhesives, both permanent or temporary, may be used including, for example, contact adhesives, pressure sensitive adhesives, glues, epoxies, adhesive resins, and the like.

Typically, the housing 45 is at least water resistant to prevent the flow of fluids into contact with the components in the housing, including, for example, the conductive contacts 80. Preferably, the housing is waterproof In one embodiment, two or more components of the housing 45, for example, the base 74 and the cover 76, fit together tightly to form a hermetic, waterproof, or water resistant seal so that fluids can not flow into the interior of the on-skin sensor control unit 44. This may be useful to avoid corrosion currents and/or degradation of items within the on-skin sensor control unit 44, such as the conductive contacts, the battery, or the electronic components, particularly when the patient engages in such activities as showering, bathing, or swimming.

Water resistant, as used herein, means that there is no penetration of water through a water resistant seal or housing when immersed in water at a depth of one meter at sea level. Waterproof, as used herein, means that there is no penetration of water through the waterproof seal or housing when immersed in water at a depth of ten meters, and preferably fifty meters, at sea level. It is often desirable that the electronic circuitry, power supply (e.g., battery), and conductive contacts of the on-skin sensor control unit, as well as the contact pads of the sensor, are contained in a water resistant, and preferably, a waterproof, environment.

The on-skin sensor control unit 44 is typically attached to the skin 75 of the patient, as illustrated in FIG. 8. The on-skin sensor control unit 44 may be attached by a variety of techniques including, for example, by adhering the on-skin sensor control unit 44 directly to the skin 75 of the patient with an adhesive provided on at least a portion of the housing 45 of the on-skin sensor control unit 44 which contacts the skin 75, by suturing the on-skin sensor control unit 44 to the skin 75 through suture openings (not shown) in the sensor control unit 44, or by strapping the on-skin sensor control unit 44 to the skin 75.

Another method of attaching the housing 45 of the on-skin sensor control unit 44 to the skin 75 includes using a mounting unit, 77. The mounting unit 77 is often a part of the on-skin sensor control unit 44. One example of a suitable mounting unit 77 is a double-sided adhesive strip, one side of which is adhered to a surface of the skin of the patient and the other side is adhered to the on-skin sensor control unit 44. In this embodiment, the mounting unit 77 may have an optional opening 79 which is large enough to allow insertion of the sensor 42 through the opening 79. Alternatively, the sensor may be inserted through a thin adhesive and into the skin.

A variety of adhesives may be used to adhere the on-skin sensor control unit 44 to the skin 75 of the patient, either directly or using the mounting unit 77, including, for example, pressure sensitive adhesives (PSA) or contact adhesives. Preferably, an adhesive is chosen which is not irritating to all or a majority of patients for at least the period of time that a particular sensor 42 is implanted in the patient. Alternatively, a second adhesive or other skin-protecting compound may be included with the mounting unit so that a patient, whose skin is irritated by the adhesive on the mounting unit 77, can cover his skin with the second adhesive or other skin-protecting compound and then place the mounting unit 77 over the second adhesive or other skin-protecting compound. This should substantially prevent the irritation of the skin of the patient because the adhesive on the mounting unit 77 is no longer in contact with the skin, but is instead in contact with the second adhesive or other skin-protecting compound.

Returning to FIG. 8, when the sensor 42 is changed, the on-skin sensor control unit 44 may be moved to a different position on the skin 75 of the patient, for example, to avoid excessive irritation. Alternatively, the on-skin sensor control unit 44 may remain at the same place on the skin of the patient until it is determined that the unit 44 should be moved.

Another embodiment of a mounting unit 77 used in an on-skin sensor control unit 44 is illustrated in FIGS. 10A and 10B. The mounting unit 77 and a housing 45 of an on-skin sensor control unit 44 are mounted together in, for example, an interlocking manner, as shown in FIG. 10A. The mounting unit 77 is formed, for example, using plastic or polymer materials, including, for example, polyvinyl chloride, polyethylene, polypropylene, polystyrene, ABS polymers, and copolymers thereof. The mounting unit 77 may be formed using a variety of techniques including, for example, injection molding, compression molding, casting, and other molding methods.

The mounting unit 77 typically includes an adhesive on a bottom surface of the mounting unit 77 to adhere to the skin of the patient or the mounting unit 77 is used in conjunction with, for example, double-sided adhesive tape or the like. The mounting unit 77 typically includes an opening 79 through which the sensor 42 is inserted, as shown in FIG. 10B. The mounting unit 77 may also include a support structure 220 for holding the sensor 42 in place and against the conductive contacts 80 on the on-skin sensor control unit 42. The mounting unit 77, also, optionally, includes a positioning structure 222, such as an extension of material from the mounting unit 77, that corresponds to a structure (not shown), such as an opening, on the sensor 42 to facilitate proper positioning of the sensor 42, for example, by aligning the two complementary structures.

In another embodiment, a coupled mounting unit 77 and housing 45 of an on-skin sensor control unit 44 is provided on an adhesive patch 204 with an optional cover 206 to protect and/or confine the housing 45 of the on-skin sensor control unit 44, as illustrated in FIG. 11A. The optional cover may contain an adhesive or other mechanism for attachment to the housing 45 and/or mounting unit 77. The mounting unit 77 typically includes an opening 49 through which a sensor 42 is disposed, as shown in FIG. 11B. The opening 49 may optionally be configured to allow insertion of the sensor 42 through the opening 49 using an introducer 120 or insertion gun 200

(see FIG. 9). The housing 45 of the on-skin sensor control unit 44 has a base 74 and a cover 76, as illustrated in FIG. 11C. A bottom view of the housing 45, as shown in. FIG. 11D, illustrates ports 230 through which conductive contacts (not shown) extend to connect with contact pads on the sensor 42. A board 232 for attachment of circuit components may optionally be provided within the on-skin sensor control unit 44, as illustrated in FIG. 11E.

In some embodiments, the adhesive on the on-skin sensor control unit 44 and/or on any of the embodiments of the mounting unit 77 is water resistant or waterproof to permit activities such as showering and/or bathing while maintaining adherence of the on-skin sensor control unit 44 to the skin 75 of the patient and, at least in some embodiments, preventing water from penetrating into the sensor control unit 44. The use of a water resistant or waterproof adhesive combined with a water resistant or waterproof housing 45 protects the components in the sensor control unit 44 and the contact between the conductive contacts 80 and the sensor 42 from damage or corrosion. An example of a non-irritating adhesive that repels water is Tegaderm (3M, St. Paul, Minn.).

In one embodiment, the on-skin sensor control unit 44 includes a sensor port 78 through which the sensor 42 enters the subcutaneous tissue of the patient, as shown in FIGS. 5 to 7. The sensor 42 may be inserted into the subcutaneous tissue of the patient through the sensor port 78. The on-skin sensor control unit 44 may then be placed on the skin of the patient with the sensor 42 being threaded through the sensor port 78. If the housing 45 of the sensor 42 has, for example, a base 74 and a cover 76, then the cover 76 may be removed to allow the patient to guide the sensor 42 into the proper position for contact with the conductive contacts 80.

Alternatively, if the conductive contacts 80 are within the housing 45 the patient may slide the sensor 42 into the housing 45 until contact is made between the contact pads 49 and the conductive contacts 80. The sensor control unit 44 may have a structure which obstructs the sliding of the sensor 42 further into the housing once the sensor 42 is properly positioned with the contact pads 49 in contact with the conductive contacts 80.

In other embodiments, the conductive contacts 80 are on the exterior of the housing 45 (see e.g., FIGS. 10A-10B and 11A-11E). In these embodiments, the patient guides the contacts pads 49 of the sensor 42 into contact with the conductive contacts 80. In some cases, a guiding structure may be provided on the housing 45 which guides the sensor 42 into the proper position. An example of such a structure includes a set of guiding rails extending from the housing 45 and having the shape of the sensor 42.

In some embodiments, when the sensor 42 is inserted using an introducer 120 (see FIG. 3), the tip of the introducer 120 or optional insertion gun 200 (see FIG. 9) is positioned against the skin or the mounting unit 77 at the desired insertion point. In some embodiments, the introducer 120 is positioned on the skin without any guide. In other embodiments, the introducer 120 or insertion gun 200 is positioned using guides (not shown) in the mounting unit 77 or other portion of the on-skin sensor control unit 44. In some embodiments, the guides, opening 79 in the mounting unit 77 and/or sensor port 78 in the housing 45 of the on-skin sensor control unit 44 have a shape which is complementary to the shape of the tip of the introducer 120 and/or insertion gun 200 to limit the orientation of the introducer 120 and/or insertion gun 200 relative to the opening 79 and/or sensor port 78. The sensor can then be subcutaneously inserted into the patient by matching the complementary shape of the opening 79 or sensor port 78 with the introducer 120 and/or insertion gun 200.

In some embodiments, the shapes of a) the guides, opening 79, or sensor port 78, and (b) the introducer 120 or insertion gun 200 are configured such that the two shapes can only be matched in a single orientation. This aids in inserting the sensor 42 in the same orientation each time a new sensor is inserted into the patient. This uniformity in insertion orientation may be required in some embodiments to ensure that the contact pads 49 on the sensor 42 are correctly aligned with appropriate conductive contacts 80 on the on-skin sensor control unit 44. In addition, the use of the insertion gun, as described above, may ensure that the sensor 42 is inserted at a uniform, reproducible depth.

An exemplary on-skin sensor control unit 44 can be prepared and used in the following manner. A mounting unit 77 having adhesive on the bottom is applied to the skin. An insertion gun 200 (see FIG. 9) carrying the sensor 42 and the introducer 120 is positioned against the mounting unit 77. The insertion gun 200 and mounting unit 77 are optionally designed such that there is only one position in which the two properly mate. The insertion gun 200 is activated and a portion of the sensor 42 and optionally a portion of the introducer 120 are driven through the skin into, for example, the subcutaneous tissue. The insertion gun 200 withdraws the introducer 120, leaving the portion of the sensor 42 inserted through the skin. The housing 45 of the on-skin control unit 44 is then coupled to the mounting unit 77. Optionally, the housing 45 and the mounting unit 77 are formed such that there is only one position in which the two properly mate. The mating of the housing 45 and the mounting unit 77 establishes contact between the contact pads 49 (see e.g., FIG. 2) on the sensor 42 and the conductive contacts 80 on the on-skin sensor control unit 44. Optionally, this action activates the on-skin sensor control unit 44 to begin operation.

The introducer, sensor, insertion gun and mounting unit can be manufactured, marketed, or sold as a unit. For example, FIG. 12 depicts an introducer 270, sensor 272, insertion gun 274 and mounting unit 276, which can be assembled (as indicated by the arrows) and sold together in an insertion kit. In such an embodiment of an insertion kit, the insertion gun 274 can be packaged in a pre-loaded fashion, with an introducer 270 and sensor 272 mated or otherwise coupled, the mated sensor 272 and introducer 270 loaded upon the carrier 278 of the insertion gun, and with a mounting unit 276 already mated with the end of the insertion gun 274.

In one embodiment, the insertion gun 274 is packaged in a state where it is ready to thrust the sensor 272 (and perhaps introducer 270) into subcutaneous tissue. For example, the insertion gun 274 can be packaged in a "cocked" state, such that the thrusting force used to introduce the sensor 272 into the subcutaneous tissue is stored in the device as potential energy (in the case of the embodiment depicted in FIG. 12, the insertion gun 274 would be "cocked" by compressing its spring 280, thus storing potential energy within the coils of the spring). Preferably, an insertion gun 274 packaged in such a manner employs a "safety", a barrier to prevent the release of the stored potential energy. The barrier is removed in order to permit the potential energy to be released. Within the context of the embodiment presented in FIG. 12, an example of a safety is a pin (not pictured) that impedes the spring from expanding, once compressed. Thus, an insertion kit so embodied can be obtained at a place of purchase, removed from its package, and used after removal of the safety, without necessitating additional steps. Alternatively, the insertion gun 274 can be packaged in the above-described pre-loaded configuration, but without being "cocked". Thus, an insertion kit with an "uncocked" insertion gun 274 can be obtained at a place of purchase, removed from its package, cocked, and used. To facilitate the insertion kit being ready to use with minimal user-exercised steps, the insertion kit can be sterilized prior to packaging. Examples of acceptable sterilizing techniques include exposing the elements of the insertion kit to gamma radiation or an e-beam.

Referring to FIGS. 13-33, preferred commercial embodiments of a sensor inserter constructed according to the invention will now be described. FIG. 13 shows an overall perspective view of a sensor inserter kit 300 comprising a single-use sensor inserter 310 and a single-use adhesive mount 312 removably attached to the bottom thereof.

As an overview of the operation of inserter kit 300, the kit comes packaged generally as shown in FIG. 13 with a sensor 314 (best seen in FIGS. 16 and 25) preloaded within inserter 310 and with inserter 310 in a "cocked" state. After preparing an insertion site on the skin, typically in the abdominal region, the patient removes upper liner 316 and lower liner 318 from adhesive mount 312 to expose the bottom surface and a portion of the top surface of an adhesive tape 320 (best seen in FIG. 16) located beneath mount 312. Mount 312, with inserter 310 attached, is then applied to the patient's skin at the insertion site. Safety lock tabs 322 are squeezed together to allow actuator button 324 to be pressed causing inserter 310 to fire, thereby inserting sensor 314 into the patient's skin with a predetermined velocity and force. Once sensor 314 has been inserted into the skin, the patient removes inserter 310 from mount 312 by pressing release tabs 326 on opposite sides of inserter 310 and lifting inserter 310 away from mount 312.

Referring to FIG. 14, mount 312 is shown adhered to a patient's skin 328 with sensor 314 already inserted. Once inserter 310 is removed from mount 312, transmitter 330 can be slid into place. The circuitry of transmitter 330 makes electrical contact with the contact pads on sensor 314 after transmitter 330 is fully seated on mount 312. Once initialization and synchronization procedures are completed, electrochemical measurements from sensor 314 can be sent wirelessly from transmitter 330 to a portable receiver 332, as shown in FIG. 15. Sensor 314, mount 312 and transmitter 330 remain in place on the patient for a predetermined period, currently envisioned to be three days. These components are then removed so that sensor 314 and mount 312 can be properly discarded. The entire procedure above can then be repeated with a new inserter 310, sensor 314 and mount 312, reusing transmitter 330 and receiver 332.

Referring to FIG. 16, the preferred inserter kit 300 is assembled as shown from the following components: housing 334, actuator button 324, drive spring 336, shuttle 338, introducer sharp 340, sensor 314, retraction spring 342, inserter base 344, upper liner 316, adhesive mount 312, adhesive tape 320, and lower liner 318.

Sensor 314 has a main surface 346 slidably mounted between U-shaped rails 348 of introducer sharp 340 and releasably retained there by sensor dimple 350 which engages introducer dimple 352. Introducer sharp 340 is mounted to face 354 of shuttle 338, such as with adhesive, heat stake or ultrasonic weld. Sensor 314 also has a surface 356 that extends orthogonally from main surface 346 and just beneath a driving surface 358 of shuttle 338 when mounted thereon (details of these features are better shown in FIGS. 19 and 25-27.)

Shuttle 338 is slidably and non-rotabably constrained on base 344 by arcuate guides 360. As best seen in FIGS. 19, 24 and 27, shuttle 338 is generally formed by an outer ring 362 and an inner cup-shaped post 364 connected by two bridges 366. Bridges 366 slide between the two slots 368 formed between guides 360 and allow shuttle 338 to travel along guides 360 without rotating. Retraction spring 342 is captivated at its outer circumference by guides 360, at its bottom by the floor 370 of base 344, at its top by bridges 366, and at its inner circumference by the outer surface of shuttle post 364. Drive spring 336 is captivated at its bottom and outer circumference by the inside surface of shuttle post 364, at its top by the ceiling 372 inside actuator button 324, and at its inner circumference by stem 374 depending from ceiling 372. When drive spring 336 is compressed between actuator button 324 and shuttle 338 it urges shuttle 338 towards base 344. When retraction spring 342 is compressed between shuttle 338 and base 344, it urges shuttle 338 towards actuator button 324.

Actuator button 324 is slidably received within housing 334 from below and resides in opening 376 at the top of housing 334 with limited longitudinal movement. Arms 378 on each side of actuator button 324 travel in channels 380 along the inside walls of housing 334, as best seen in FIG. 20. Longitudinal movement of actuator button 324 is limited in one direction by the base 378 of arms 378 contacting the edge of opening 376 at the top of housing 334, and in the other direction by the distal ends 384 of arms 378 contacting stops 386 in channels 380. Slots 388 are preferably provided in the top of housing 334 for ease of housing manufacture and so tools can be inserted to inwardly compress arms 378 beyond stops 386 to allow actuator button 324 to be removed from housing 334 if needed.

When sensor 314, introducer 340, shuttle 338, retraction spring 342, drive spring 336 and actuator button 324 are assembled between base 344 and housing 334 as shown in FIG. 16 and described above, housing 334 is snapped into place on base 344. Base 344 is held onto housing 334 by upper base barbs 390 that engage upper openings 392 in housing 334, and lower base barbs 394 (best seen in FIG. 17) that engage lower openings 396 in housing 334. Slots 398 and 400 are provided for ease of manufacture of housing 334, and base 344 is preferably removable from housing 334 with tools if needed.

Referring to FIG. 19, actuator button 324 is preferably provided with safety lock tabs 322 hingedly formed on opposite ends. Tabs 322 can be urged from a relaxed outward position to a flexed inward position. When in the normal outward position, shoulders 402 on the outer surfaces of tabs 322 engage the rim 404 of opening 376 to prevent the actuator button 324 from being depressed, thereby avoiding accidental firing of inserter 310. Tabs 322 can be squeezed inward just enough to clear the rim 404 of opening 376 while pressing the actuator button 324 down to fire the inserter. Alternatively, tabs 322 can be squeezed further inward so that barbs 406 on the inside edges can engage catches 408 located on a center portion of actuator button 324, thereby defeating the safety lock to allow later firing by simply pressing down on the actuator button 324. Preferably, upwardly extending grips 410 are provided on tabs 322 for better visual indication of safety lock status and actuation control.

Referring to FIG. 20, shuttle 338 is provided with laterally extending barbed fingers 412 which travel in channels 380 along the inside walls of housing 334. When shuttle 338 is inserted up into housing 334 far enough, barbed fingers 412 momentarily deflect inward and then snap outward again to catch on stops 386. In this "cocked" position as shown, drive spring 336 is compressed and urging shuttle 338 towards base 344, but barbed fingers 412 catching on stops 386 prevent such travel.

Referring to FIGS. 21-23, the sequence of loading, cocking, arming, firing, and automatic retraction of inserter 310 will be described. It is envisioned that in production, inserters 310 will be fabricated and fully assembled by one vender except for sensor 314, which will be supplied and installed by a second vendor in a sterile environment. Accordingly, inserter 310 will be manufactured and shipped to the sensor vendor in a neutral state, as shown in FIG. 21. A hole 414 provided through the center of actuator button 324 allows the sensor vendor to insert a pin (manually or by automated machinery, not shown) through hole 414 to drive shuttle 338 towards base 344 in a controlled fashion and hold it there against the force of retraction spring 342. This will cause introducer sharp 340 to be extended through base 344 (as shown in FIG. 23) so that sensor 314 can be loaded into introducer 340. When the pin is removed, shuttle 338, introducer 340 and sensor 314 will retract to the neutral position. The sensor vendor can then cock the loaded inserter 310 before shipment by pushing another pin (not shown) from the opposite direction through a central hole 416 in base 344 (with mount 312 removed) until the pin contacts dimple 418 formed in the bottom of shuttle 338. By pushing shuttle 338 towards actuator button 324 until barbed fingers 412 clear stops 386, the inserter 310 is cocked (as shown in FIG. 22.)

Referring to FIG. 22, inserter 310 is preferably received by the patient in the cocked position as shown. To use inserter 310, the patient applies mount 312 to the mounting site and disables the safety mechanism as previously described, and then pushes actuator button 324 against the force of drive spring 336. As actuator button 324 travels toward base 344, drive cam surfaces 420 on arms 378 contact ramped surfaces 422 of barbed fingers 412 and urge them inward. When fingers 412 are driven inward enough to clear stops 386, shuttle 338 is driven by drive spring 336 with a predetermined speed and force to an insertion position, as shown in FIG. 23.

Referring to FIG. 23, inserter 310 is shown in the insertion position with the tail 424 of introducer sharp 340 extending through base 344 and mount 312 into the skin of the patient. FIG. 23 shows shuttle 338 in a fully extended position with its lower surface 426 bottomed out on base 344. However, the lower orthogonal surface 356 of sensor 314 will contact an exposed sensor contact portion 428 (best seen in FIGS. 14 and 16) on top of adhesive tape 320 supported from below by the patient's skin, and therefore will typically stop traveling before reaching the fully bottomed out position shown. Tail 424 of introducer sharp 340 provides rigidity and a skin piercing edge 430 for allowing the flexible tail 431 of sensor 314 to be implanted in the patient's skin. After providing this function, introducer sharp 340 is immediately removed from the patient and retracted into a safe position inside housing 334 as retraction spring 342 (which has been compressed by the travel of the shuttle) pushes shuttle 338 back towards actuator cap. Sensor 314 is pulled from introducer 340 and held in place by the sensor contact portion 428 on top of adhesive tape 320 adhering to orthogonal surface 356 of sensor 314. The geometries of sensor dimple 350 and mating introducer dimple 352 are chosen to create a separation force between them that is less than the adhesion force of tape 320 on orthogonal surface 356, but great enough to retain sensor 314 in introducer 340 during typical shipping and product handling shock loads. Driving surface 358 beneath shuttle 338 presses down on top of orthogonal surface 356 to ensure good contact with adhesive tape 320 before shuttle 338 retracts with introducer 340. As discussed above with previous embodiments, barb(s) on sensor tail 431 can be employed to further anchor the sensor in its operating position.

Referring again to FIG. 21, retraction spring 342 will return shuttle 338 to the neutral position as shown after firing, but without sensor 314 which remains inserted in patient's skin (not still in introducer 340 as shown here.) Drive spring 336 is preferably designed to be stiffer than retraction spring 342 so that shuttle 338 oscillations are quickly dampened out, and so introducer sharp 340 does not return to sensor 314 or the patient to cause injury. With sensor 314 now inserted in the patient's skin, inserter 310 can be removed from mount 312 by inwardly flexing release tabs 326 on opposite sides of inserter 310 to remove latch hooks 432 from mount channels 434 and then lifting inserter 310 away from mount 312. Introducer sharp 340 remains protected inside housing 334 during disposal of inserter 310. Transmitter 330 can now be slid into place on mount 312 as previously described.

Referring to FIG. 28, an alternative embodiment of adhesive tape 320' is shown. This oversized tape 320' has the advantage of holding transmitter 330 in place even when fairly large forces are placed on it. In this embodiment adhesive tape 320' has a double-sided portion 436. (adhesive on both top and bottom sides) residing between mount 312 and the patient's skin, and a single-sided portion 438 outwardly extending from the double-sided portion 436, preferably in all directions, for adhering just to the patient's skin. In the previous embodiment, it is difficult to separate mount .312 from the skin merely with tension forces, but applying a force to just one side of mount 312 results in a high peeling force being applied to that edge of the adhesive tape 320 which causes tape 320 to peel off of the skin. In contrast, any force applied to transmitter 330 in this alternative embodiment results in a tension force rather than a peeling force being applied to tape 320', inhibiting inadvertent removal until an edge of tape 320' is intentionally peeled up. Preferably, single-sided portion 438 has a width roughly double the width of double-sided portion 436. In the preferred embodiment, theses widths are 2.14 and 1.14 inches, respectively. Preferably, the length that single-sided portion 438 extends beyond double-sided portion 436 is roughly equivalent to the combined height of transmitter 330 attached to mount 312, in this case about 0.5 inches.

In the preferred embodiment, sensor 314 is made from a 0.005 inch thick Mylar substrate, such as Dupont Melinex ST-505, print treated both sides, heat stabilized and bi-axially oriented. Main surface 346 is 0.315 tall by 0.512 wide, and orthogonal surface 356 is 0.374 wide by 0.202 deep. Sensor tail 431 is 0.230 long by 0.023 wide. Semispherical sensor dimple 350 is 0.050 inches wide and 0.026 inches deep. Introducer 340 is made from SUS 301 medical grade stainless steel, 0.004 inches thick, having a surface roughness less than or equal to 0.5 micrometers. The height of the main portion of introducer 340 is 0.614 inches, and the inside width is 0.513 inches. The overall thickness of rolled rails 348 is 0.026 inches. The length and width of introducer tail 424 are 0.354 and 0.036 inches, respectively. The preferred angle of the sharp 340 is 21 degrees. Preferably, semispherical introducer dimple 352 has a radius of 0.024 inches. In the preferred embodiment, shuttle 338 has an average speed of at least 1 meter/second, and has a momentum at its end of travel of about 2.65 lb-m/sec.

Preferably, housing 334, button 324, shuttle 338, base 344 and mount 312 are all injection molded from G.E. Lexan PC. Inside and outside working surfaces of arms 378 on button 324 are preferably lubricated with Dow Corning 360 Medical Fluid. Drive spring 336 has a free length of 1.25 inches, a working length of 1.00 inch, and a rate between 20 and 30 pounds per inch. Retraction spring 342 has a free length of 1.5 inches, a working length of 0.35 inches, and a rate between 0.15 and 0.35 pounds per inch. Adhesive tape 320 preferably is medical grade acrylic adhesive on polyester film (such as Acutek 0396013) with a semi-bleached kraft liner having silicon release.

Referring to FIG. 29, an interconnect 440 is shown for providing waterproof electrical connections between sensor 314 and transmitter 330. Interconnect 440 includes a seal 442 mounted on an end of transmitter 330 that contacts one side of sensor 314 when transmitter 330 is slid onto mount 312. When transmitter 330 is locked into place on mount 312, seal 442 is compressed between transmitter 330 and sensor 314 and urges sensor 314 against raised end stop 444 of mount 312.

Referring to FIG. 30, further details of interconnect 440 are shown. Seal 442 has an exterior wall 446 for surrounding electrical contacts 448 (in this case four), and interior walls 450 for isolating electrical contacts 448 from each other. Rim 452 formed on the transmitter housing 330 surrounds the base 454 of seal 442 to prevent it from collapsing outward when compressed.

Referring to FIG. 31, an enlarged partial view of FIG. 30 is shown with seal 442 and one spring removed for clarity. Electrical contacts 448 are preferably constructed from compression springs 456 mounted on connector lugs 458. Lugs 458 are stamped rearward on their edges to form protrusions 460 that retain springs 456. Alternately or in conjunction with this stamping, plastic rings (not shown) can be melted over the base of each spring 456 for attaching it to its respective lug 458. Connector lugs 458 can protrude through slots in transmitter housing 330, or be insert molded integral with the plastic housing 330 when it is molded.

Referring to FIG. 32, and enlarged perspective view of the seal 442 is shown. It has been discovered through experimentation that two lips 462 of equal height along the distal edge of exterior wall 446 provide the best seal from exterior elements. Good isolation between electrical contacts 448 is best achieved by having interior walls 450 with a height equal to that of lips 462. Recesses 464 should be sized large enough so that seal 442 does not interfere with the movement of springs 456 when seal 442 and springs 456 are compressed. In the preferred embodiment, the distal face of seal 442 defined by lips 462 is formed at a 1 degree angle to match the draft angle of mount end stop 444.

Seal 442 is preferably made of shore A 30 durometer compression molded silicone. It is envisioned that seal 442 can be shortened in the axial direction (parallel to springs 456) to reduce the force required to compress it when attaching transmitter 330 to mount 312. Best results for fastening seal 442 to transmitter housing 330 have been achieved with double sided adhesive tape 320, silicone adhesive on one side and acrylic adhesive on the other for sticking to the PC-ABS blend of the transmitter housing 330, such as product number 9731 manufactured by 3M Company of St. Paul, Minn. Springs 456 are preferably made from gold-plated beryllium copper so as to deter galvanic current effects. Preferably, main surface 346 of sensor 314 that contacts seal 442 has a uniform thickness dielectric coating with a window in it (i.e. no dielectric) where springs 456 contact sensor 314. An interconnect 440 constructed as described above remains water proof when submerged to a depth of at least 1 meter for 45 minutes.

To increase the reliability of sensor insertion, the following enhancements can be added to the inserter kit 300 described above. First, a sensor flap 466, as shown in FIG. 25, can be formed along the top edge of sensor 314. When sensor 314 reaches the extended, delivered position as shown in FIG. 23, flap 466 catches on bottom edge 468 of base 344, shown in FIG. 19, to ensure that sensor 314 separates from introducer 340 as shuttle 338 returns upward to the retracted position. Adhesive can also be located on the bottom of orthogonal sensor surface 356 to ensure that sensor 314 adheres to the sensor contact portion 428 on the top of adhesive mount tape 320, as shown in FIG. 16.

Referring to FIGS. 33A and 33B, actuator button 324' can be made easier for elderly patients to push by anchoring the upper end of drive spring 336 on a housing bridge 470 instead of button 324. This change also makes the insertion force of inserter 310 more consistent, and allows stronger spring forces to be used if desired. Bridge 470 spans across opening 376' and divides it into two openings 472 in the top of housing 334'. The top portion of button 324' is bifurcated into two protrusions 474 that each extend through an opening 472. A clearance hole (not shown) is provided through the center of button 324' to allow drive spring 336 to pass through and secure around a post (not shown) depending from the bottom center of bridge 470.

Safety lock key 476 can be provided to prevent actuator button 324' from being pressed until key 476 is removed. Aperture 478 is provided in the top center of bridge 470 for receiving boss 480 located at the bottom of key 476, thereby allowing key 476 to rotate. When key handle 482 is rotated perpendicular to button protrusions 474 as shown, two opposing perpendicular fins 484 on key 476 swing into inwardly facing slots (not shown) on the inside of protrusions 474 and prevent button 324' from being actuated. When key handle 482 and fins 484 are rotated parallel to button protrusions 474 such that fins 484 disengage therefrom, key 476 can be removed and button 324' can then be actuated. Other than these modifications, this inserter kit 300' functions the same as the embodiment previous described.

To provide an easier and more consistent release of shuttle 338 by actuator button 324 or 324', it is envisioned that less aggressive finger engagement with stops 386 can be employed, or the above designs can be modified to have a single, more centrally located shuttle release finger (not shown) instead of the two outboard fingers 412 shown.

The present invention should not be considered limited to the particular examples described above. Various modifications, equivalent processes, as well as numerous structures to which the present invention may be applicable and which fall within the general scope of the invention will be readily apparent to those of skill in the art to which the present invention is directed upon review of the instant specification.

The invention claimed is:

1. A sensor inserter assembly comprising:
a housing detachably coupled to a mount;
an analyte sensor;
an introducer sharp having a retention element disposed on a planar surface for releasably retaining the analyte sensor; and
an actuator moving the introducer sharp and the analyte sensor in an insertion direction from within the housing to an extended position in which at least a portion of the introducer sharp and at least a portion of the analyte sensor protrude from the housing, the mount maintained in a fixed position relative to the housing while the introducer sharp moves in the insertion direction, the at least the portion of the analyte sensor adapted to be maintained in fluid contact with an analyte at the extended position, the actuator being automatically moved in a retraction direction when the at least the portion of the introducer sharp and the at least the portion of the analyte sensor protrude from the housing, wherein moving the actuator in the retraction direction causes the introducer sharp to move in the retraction direction from the extended position to a retracted position in which the introducer sharp is retracted entirely within the housing and separated from the analyte sensor, the analyte sensor detaching from the retention element of introducer sharp when the actuator moves the introducer sharp in the retraction direction, wherein the distance between the extended position and the retracted position is a fixed distance;
wherein the actuator is axially aligned with the sensor and the introducer sharp along the insertion and retraction directions.

2. The assembly of claim 1 wherein the analyte sensor includes a glucose sensor.

3. The assembly of claim 1 wherein the actuator includes a manual actuator for applying a manual force to move the introducer sharp in the insertion direction.

4. The assembly of claim 1 wherein the actuator includes a manual actuator for applying a manual force to move the introducer sharp in the retraction direction.

5. The assembly of claim 1 wherein the actuator includes a spring for applying a spring biased force to automatically move the introducer sharp in the insertion direction or in the retraction direction.

6. The assembly of claim 1 wherein the insertion direction is at an angle of approximately 90 degrees or less relative to the skin layer.

7. The assembly of claim 1 wherein the mount is detached from the housing after the introducer sharp is retracted within the housing and separated from the sensor.

8. A method, comprising:
detachably coupling a housing to a mount;
providing an analyte sensor;
providing an introducer having at least one cutting portion for releasably receiving the analyte sensor;
disposing a retention element on a planar surface of at least one of the introducer or the analyte sensor to releasably retain at least a portion of the analyte sensor adjacent to the introducer;
coupling an actuator to the introducer to displace the sensor and introducer in an insertion direction to an extended position in which at least a portion of the introducer and the analyte sensor protrude from the housing to pierce through a skin layer prior to reaching the extended position, coupling the actuator to the introducer including axially aligning the actuator with the analyte sensor and the introducer along the insertion and retraction directions; and
maintaining the mount at a fixed position relative to the housing when the introducer and the analyte sensor are displaced in the insertion direction to the extended position, the introducer automatically moving in a retraction direction from the extended position to a retracted position when the retention element releases the sensor from the introducer, the introducer being retracted within the housing when in the retracted position such that the introducer is retained entirely within the housing and physically separated from the analyte sensor.

9. The method of claim 8, wherein receiving the analyte sensor within the introducer includes slidably receiving the analyte sensor.

10. The method of claim 8, further comprising providing a safety to impede the actuator until the safety is deactivated.

11. The method of claim 8 wherein the actuator includes a manual actuator and displacing the introducer and the analyte sensor in the insertion direction comprises applying a manual force to move the introducer in the insertion direction.

12. The method of claim 8 wherein the actuator includes a manual actuator and moving the introducer in the retraction direction comprises applying a manual force to move the introducer in the retraction direction.

13. The method of claim 8 wherein the insertion direction is at an angle of approximately 90 degrees or less relative to the skin layer.

14. The method of claim 8 further comprising detaching the mount from the housing when the introducer is at the retracted position within the housing and separated from the analyte sensor.

15. The method of claim 8 further comprising coupling the mount to the housing prior to moving the sensor and the introducer to the extended position.

16. A sensor inserter assembly comprising:
a housing detachably coupled to a mount;
a sensor;
an introducer sharp having at least one cutting portion and arranged for releasably receiving the sensor;
a retention element disposed on a planar surface of at least one of the introducer sharp or the sensor, the retention element configured to releasably retain at least a portion of the sensor adjacent to the introducer sharp; and
an actuator coupled to the introducer sharp to move the sensor and introducer sharp in an insertion direction to an extended position in which at least a portion of the introducer sharp and the sensor protrude from the housing to pierce through a skin layer prior to reaching the extended position, the position of the mount maintained at a fixed position relative to the housing when the introducer sharp and the sensor move in the insertion direction to the extended position, the introducer sharp automatically moving in a retraction direction from the extended position to a retracted position when the retention element releases the sensor from the introducer sharp, the introducer sharp being retracted within the housing when in the retracted position such that the introducer sharp is retained entirely within the housing and physically separated from the sensor;
wherein the actuator is axially aligned with the sensor and the introducer sharp along the insertion and retraction directions.

17. The assembly of claim 16 wherein the sensor includes an analyte sensor.

18. The assembly of claim 17 wherein the analyte sensor includes a glucose sensor.

19. The assembly of claim 16 wherein the actuator includes a manual actuator for applying a manual force to move the introducer sharp in the insertion direction.

20. The assembly of claim 16 wherein the actuator includes a manual actuator for applying a manual force to move the introducer sharp in the retraction direction.

21. The assembly of claim 16 wherein the actuator includes a spring for applying a spring biased force to automatically move the introducer sharp in the insertion direction or in the retraction direction.

22. The assembly of claim 16 wherein the insertion direction is at an angle of approximately 90 degrees or less relative to the skin layer.

23. The assembly of claim 16 wherein the housing, the sensor, the introducer sharp, the retention element and the actuator are single use components.

24. The assembly of claim 16 wherein the mount is detached from the housing when the introducer sharp is at the retracted position within the housing and separated from the sensor.

25. The assembly of claim 16 wherein the mount is coupled to the housing prior to moving the sensor and the introducer sharp to the extended position.

26. The sensor inserter assembly of claim 16, wherein the sensor is slidably received within the introducer sharp.

27. The sensor inserter assembly of claim 16, wherein the assembly further comprises a safety to impede the actuator until the safety is deactivated.

28. The assembly of claim 16 wherein the sensor includes a transcutaneous sensor.

* * * * *